(12) United States Patent  (10) Patent No.: US 8,676,607 B2
Patel et al.  (45) Date of Patent: Mar. 18, 2014

(54) OBTAINING PATIENT SURVEY RESULTS

(75) Inventors: Bimal Vinod Patel, San Diego, CA (US); Cynthia Chiyemi Yamaga, Oceanside, CA (US); Louis Leo Brunetti, Encinitas, CA (US)

(73) Assignee: MedImpact Healthcare Systems, Inc.

( * ) Notice: Subject to any disclaimer, the term of this patent is extended or adjusted under 35 U.S.C. 154(b) by 487 days.

(21) Appl. No.: 12/987,993

(22) Filed: Jan. 10, 2011

(65) Prior Publication Data
US 2012/0179480 A1 Jul. 12, 2012

(51) Int. Cl.
*G06Q 50/00* (2012.01)

(52) U.S. Cl.
USPC .................................................. 705/3; 705/2

(58) Field of Classification Search
USPC ........................................................ 705/2, 3
See application file for complete search history.

(56) References Cited

U.S. PATENT DOCUMENTS

| | | | |
|---|---|---|---|
| 6,578,003 B1 * | 6/2003 | Camarda et al. | 705/3 |
| 7,319,970 B1 * | 1/2008 | Simone | 705/4 |
| 7,505,917 B2 | 3/2009 | Howe et al. | |
| 7,809,585 B1 | 10/2010 | Ghouri | |
| 8,100,829 B2 * | 1/2012 | Rothman et al. | 600/300 |
| 8,346,571 B2 | 1/2013 | Kalies | |
| 2002/0128866 A1 * | 9/2002 | Goetzke et al. | 705/2 |
| 2003/0135392 A1 | 7/2003 | Vrijens et al. | |
| 2005/0108051 A1 | 5/2005 | Weinstein | |
| 2006/0184391 A1 | 8/2006 | Barre et al. | |
| 2006/0184493 A1 | 8/2006 | Shiffman et al. | |
| 2006/0218011 A1 | 9/2006 | Walker et al. | |
| 2007/0250341 A1 | 10/2007 | Howe et al. | |
| 2008/0091475 A1 | 4/2008 | Sottile | |
| 2008/0109252 A1 * | 5/2008 | LaFountain et al. | 705/2 |
| 2008/0147438 A1 | 6/2008 | Kil | |
| 2008/0312956 A1 | 12/2008 | Momita et al. | |
| 2008/0319272 A1 | 12/2008 | Patangay et al. | |
| 2009/0171697 A1 | 7/2009 | Glauser et al. | |
| 2009/0247834 A1 * | 10/2009 | Schechter | 600/300 |
| 2010/0100392 A1 * | 4/2010 | Rothman et al. | 705/2 |
| 2010/0205008 A1 | 8/2010 | Hua et al. | |
| 2011/0010328 A1 | 1/2011 | Patel et al. | |
| 2011/0093288 A1 * | 4/2011 | Soto et al. | 705/2 |
| 2011/0105852 A1 * | 5/2011 | Morris et al. | 600/300 |

(Continued)

FOREIGN PATENT DOCUMENTS

WO  WO2008089084 A2  7/2008

OTHER PUBLICATIONS

Lee, Chung Keun, Authorized Officer, Korean Intellectual Property Office, International Application No. PCT/US2010/041426 / filed Jul. 8, 2010, in International Search Report and Written Opinion, mailed Feb. 15, 2011, 10 pages.

(Continued)

*Primary Examiner* — Elaine Gort
*Assistant Examiner* — Jonathan K Ng
(74) *Attorney, Agent, or Firm* — Fish & Richardson P.C.

(57) ABSTRACT

Systems and techniques are disclosed for determining a health risk assessment score for a patient who did not complete a health risk assessment. In some implementations, the health risk assessment score can be determined for the patient who did not respond based on a behavior prediction score obtained for the patient who did not respond, behavior prediction scores for patients who did respond to the health risk assessment, and health risk assessment scores for the patients who did respond.

21 Claims, 16 Drawing Sheets

(56) References Cited

U.S. PATENT DOCUMENTS

2011/0106556 A1 5/2011 Patel et al.
2011/0178819 A1 7/2011 Mchorney
2012/0179002 A1 7/2012 Brunetti et al.
2012/0179481 A1 7/2012 Patel et al.

OTHER PUBLICATIONS

International Preliminary Report on Patentability ; Jan. 19, 2012; World Intellectual Property Organization (WIPO) (International Bureau of); PCT/US2010/041426; 7 pages.

* cited by examiner

|  | Col. A | Col. B | Col. C |
| --- | --- | --- | --- |
| *Age:* | | 65 or > | 1.60 |
| | | 55 - 65 | 1.30 |
| | | 40 - 55 | 1.20 |
| | | 25 - 40 | 1.00 |
| | | 17 -25 | 1.10 |
| | | 10 -17 | 1.20 |
| | | 0 - 10 | 1.30 |
| | | | |
| Gender | | M | 1.10 |
| | | F | 1.00 |
| | | | |
| Comorbidities | | 0 | 1.00 |
| | | 1-2 | 1.25 |
| | | 3-4 | 1.75 |
| | | 5+ | 2.00 |
| | | | |
| Adherence Score | | | |
| | *low* | 1 | 1.40 |
| | | 2 | 1.30 |
| | | 3 | 1.20 |
| | | 4 | 1.10 |
| | *high* | 5 | 1.00 |

*FIG. 14*

OBTAINING PATIENT SURVEY RESULTS

BACKGROUND

This document relates to patient surveys, and in particular, to determining results of patient surveys for patients who did not complete the surveys.

A patient survey, such as health risk assessment ("HRA"), can be provided to patients in a population to help assess risks for that population. An HRA includes questions used to assess health risks such a likelihood of a particular behavior for a patient or likelihood of an event occurring.

SUMMARY

When a patient population is given a survey, such as a HRA, many of the patients may not respond resulting in incomplete data for the population. Some patients may provide incomplete responses to the survey, also resulting in incomplete data for the population. This disclosure describes systems and techniques for determining results of a HRA for patients in a population who did not complete a survey ("non-responders") to the HRA based on results of patients in the population who did respond ("responders") to the HRA and based on behavior prediction scores determined for the patients in the population.

Each of the patients in the population can have a patient profile which includes known attributes about each of the patients. A behavior prediction score can be obtained for a patient in the patient population based on known attribute values in that patient's profile. The obtained behavior prediction score can indicate the likelihood of a particular behavior for the patient. For example, the score can include an adherence score indicating the patient's likelihood of adhering to a prescription. Also, the behavior prediction score can include a modified adherence score. For example, the modified adherence score can be for a particular application such as for risk, cost sensitivity of the patient, or disease severity.

When a patient responds to a HRA, a HRA score can be determined for the patient based on the patient's answers to the HRA. In like manner, HRA scores can be determined for all of the responders in a patient population based on each the responders' respective answers to the HRA. A HRA score is an indication of a risk being assessed by the administered HRA, such as a risk of a particular behavior or event, for the patient assigned the HRA score.

As mentioned above, a behavior prediction score is obtained based on patient characteristics and can be obtained for all of the patients in a population based on known values for those patient characteristics. The behavior predication scores can be used to determine results of a HRA for non-responders. A behavior prediction score of a non-responder can be matched with behavior prediction scores of responders. The HRA scores of the matching responders can be combined into a HRA score that is assigned to the non-responder.

One aspect of the subject matter described in this specification can be embodied in methods that include the actions of obtaining a behavior prediction score for a patient who did not complete a health risk assessment, wherein the behavior prediction score is based on attribute data for the patient; determining a health risk assessment score for the patient who did not complete the health risk assessment based on health risk assessment scores of multiple patients who did respond to the health risk assessment, the multiple patients having behavior prediction scores that correspond to the behavior prediction score of the patient who did not complete the health risk assessment, the health risk assessment score indicating a risk being assessed by the health risk assessment; and making the determined health risk assessment score available for further processing and output. Other embodiments of this aspect include corresponding systems, apparatus, and computer programs, configured to perform the actions of the methods, encoded on computer storage devices.

The details of one or more embodiments are set forth in the accompanying drawings and the description below. Other features, objects, and advantages will be apparent from the description and drawings, and from the claims.

BRIEF DESCRIPTION OF DRAWINGS

FIG. 14 shows an example of a table of attributes with associated risk weights.

DETAILED DESCRIPTION

Figure 1A:
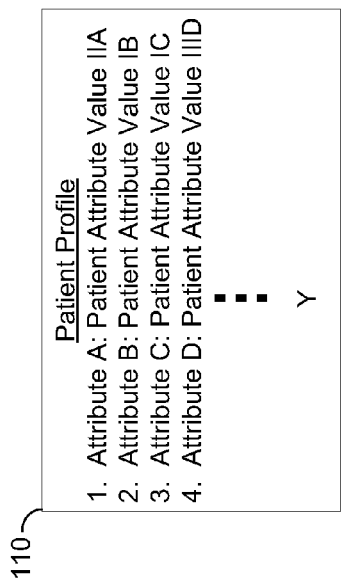
FIG. 1A shows an example patient profile that has a list of attributes for a patient.

A health risk assessment (HRA) includes questions, for which the answers are indicators of a risk being assessed by the HRA. A HRA for a particular risk can be administered to a population of patients. Patients who respond ("responders") to the HRA can be assigned an HRA score based on their respective answers to the HRA. Using the HRA scores of the responders and the behavior predication scores determined for the patients in the population, HRA scores can be determined for the non-responders (e.g., patients who did not complete the survey).

Behavior predication scores can be obtained for patients in a population, responders and non-responders alike, based on known characteristics of the patients in the population. A behavior predication score is predictor of the relative likelihood of a behavior for a patient assigned the score, such as likelihood to adhere to a prescribed treatment, likelihood of participating in a wellness program, or likelihood to respond to an intervention. A behavior predication score can also be a relative likelihood of a particular event, such a cost for treating a patient. Also, a behavior prediction score can include modified adherence scores, modified for a particular application.

As mentioned above, a type of a behavior prediction score is a patient adherence score. An adherence score can predict the relative likelihood that a patient will adhere to a prescribed treatment. For example, a patient who is more likely to adhere to a prescribed treatment can be assigned a higher score than a patient who is less likely to adhere to a prescribed treatment.

An adherence score can also predict the likelihood of non-adherence. Non-adherence can be represented by various events, examples of which include discontinuation, such as when a patient discontinues therapy, and switching, such as where a patient switches from a prescribed treatment to a different treatment (e.g. changing from a prescribed drug to a different drug). An adherence score can also be used to predict the degree to which a patient is non-adherent but persistent. For example, a patient may be non-adherent because the patient has gaps in following a prescribed treatment but persistently returns to treatment. A patient adherence score can also be specific to a particular drug, type of drug, brand, type of treatment, disease, etc. Once a score has been obtained, the score can be modified using a modifier to determine a modified score for a particular application. A modifier can be an adjustment factor for adjusting an adherence score for a particular patient into a modified score for a particular application. The modifier can be determined using a modifier algorithm for the particular application. For example, a modifier algorithm can include a set of weights that are used to weight a particular set of attributes. For a patient profile, a modifier is determined based on the weights of the algorithm and the attribute values associated with the attributes in the patient profile.

Various attributes can be used to characterize certain aspects of a patient and such characterization can be used to predict patient adherence. Attributes can include, for example, demographic factors such as gender, ethnicity, age, weight, geographic location (e.g. state breakdown, rural vs. urban etc.), socioeconomic status, educational level, economic impact variables (e.g. housing foreclosure data). Attributes can also include characteristics of a patient's medical plan, such as size of payer and type of payer (e.g., managed care organization, third party administrator, self-insured, CMS, military, etc.); design of a patient's drug benefit such as overall drug benefit, formulary design, prior authorization rules, step therapy rules, co-payment, cost of drug, availability of generic alternatives, and availability of therapeutic alternatives; or other patient related factors such as drug or alcohol abuse, health beliefs, social support, psychosocial factors, health literacy (e.g. ability to understand how to properly take a prescribed medication), perceived benefit from taking medications, perceived risk from taking medications (e.g. safety concerns due to adverse events), prior medication utilization patterns, enrollment into a clinical program (e.g. medication therapy management, disease management), consumer purchase behavior (e.g. fresh foods versus canned or frozen foods, "junk" versus "health" foods), and use of vitamins and supplements. Attributes can also include disease related factors such as disease severity, co-morbidities, and the duration of having a disease or condition; drug-related information, including drug category, number of concurrent drugs, and complexity of dosing regimen; pharmacy information such as pharmacy type (e.g. chain, independent, mail, retail, etc.), pharmacy location (e.g. rural, urban), pharmacy geographic proximity to patient, and pharmacy service (e.g. medication therapy management, vaccinations, etc.); and physician information such as physician specialty, physician geographic proximity to patient, and physician practice site.

One or more attributes can be listed in a patient profile for a patient. Each attribute has a value to quantify an aspect of the patient and a collection of the values of the one or more attributes provides a quantitative profile of the patient. FIG. 1A shows an example patient profile 110 that has a list of attributes for a patient. The patient profile 110 has Y number (1 . . . Y) of attributes, each attribute having a value. The first listed attribute, Patient Attribute A, has a Patient Attribute value IIA. The second attribute, Patient Attribute B, has a Patient Attribute Value IB. And, the third listed attribute, Patient Attribute C, has a Patient Attribute Value IC. By way of example, a patient profile 110 can have Patient Attribute A that corresponds to gender, Patient Attribute B that corresponds to weight, Patient Attribute C that corresponds to age, and Patient Attribute D that corresponds to income. Each of those attributes has a value. For a particular patient, the patient profile 110 can have the following values: Patient Attribute Value IIA can be male, Patient Attribute Value IB can be 150 pounds, patient value IC can be 50 years old, and Patient Attribute Value IIID can be low income. In a patient population, some patients can have different profiles. For example, a second patient in a population can have the following values for attributes A through B: male, 160 pounds, 40 years old, and middle income. Also, in a patient population a patient can have a profile that has the same values as another profile in the population. For example, a third patient can have the same attributes values A through B as the second patient.

In predicting patient adherence, various techniques can be used to obtain a patient adherence score. For example, a model, which can include logical and/or quantitative relationships between a specific set of attributes and likelihood of adherence, can be used to assign an adherence score. When scoring a patient profile 110 according to a model, the attribute values of the patient profile 110 that correspond to the specific set of model attributes in the model can be used to generate or assign a score. For the attributes used in the model, a mathematical algorithm can be applied to the attribute values in the patient profile for those attributes. By way of example, a particular model can use three model attributes, e.g. Attributes B, C, and D, as predictors of patient adherence. The patient profile 110 also has attributes B, C, and D. An algorithm is applied to the values of Patient Attributes B, C, and D for the patient profile 110 to produce an adherence score.

Multiple patient profiles, e.g. all of the patients in a patient population, can be scored in this manner. For example, all patients having the same insurance plan can be grouped into a patient population. According to the model discussed in the example above, each patient in the plan can be scored based on their attribute values for Attributes B, C, and D.

In some implementations of predicting patient adherence, a model can include a set of one or more model profiles where each model profile has an associated model score. In addition, each model profile can have one or more model attributes, where each model attribute has a model value. As discussed in more detail below, an adherence score can be assigned to a patient profile by matching the patient profile with one of the one of the model profiles. The adherence score associated with the matching model profile is assigned to the patient profile.

Figure 1B:
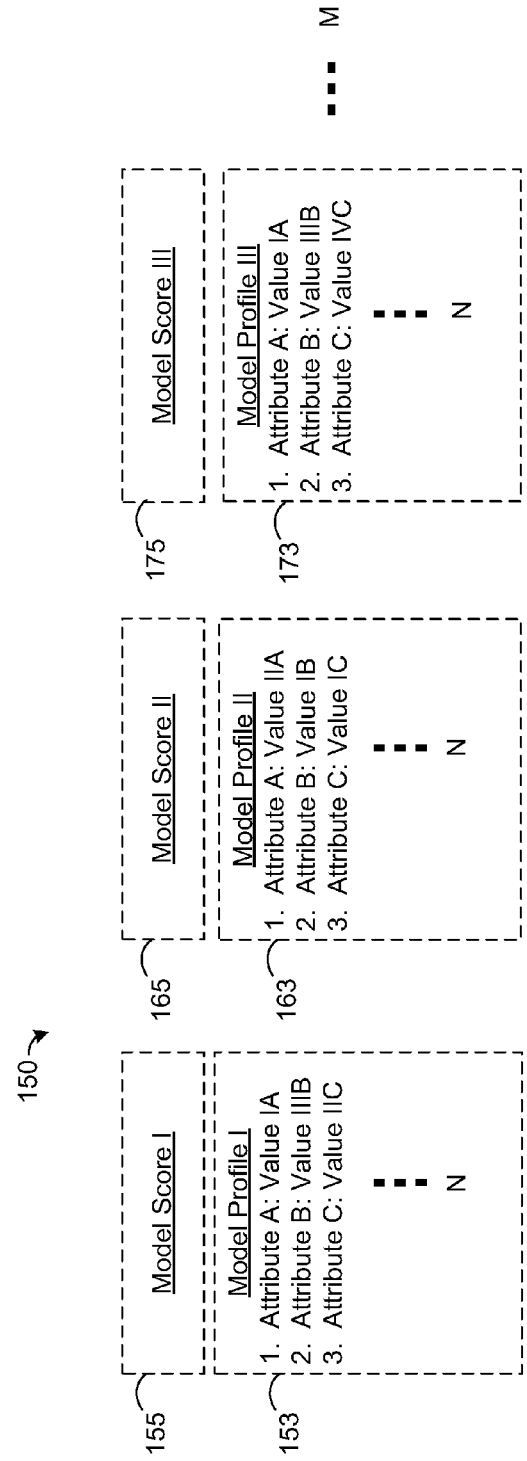
FIG. 1B shows an example model for assigning a patient adherence score.

The set of model values in each model profile can be unique. The model score can be determined for each model profile based on the unique set of model values in each model profile. FIG. 1B shows an example model 150 for assigning a patient adherence score. The model 150 includes a set of model profiles (1 ... M) and model scores associated with the model profiles. Model Profile I shown at 153 has an associated Model Score I shown at 155, Model Profile II shown at 163 has an associated Model Score II shown at 165, Model Profile III shown at 173 has an associated Model Score III shown at 175, etc.

Each model profile has 1 through N number of model attributes and each attribute has a value. Each of the model profiles has the same number and set of attributes as other model profiles but has a unique set of model values that corresponds to the model attributes. For example, Model Profile I has the following values for Attributes A-C respectively: Value IA, Value IIB, and Value IIC. Model Profile II has the following values for Attributes A-C respectively: Value IIA, Value IB, and Value IC. And, Model Profile III has the following values for Attributes A-C respectively: Value IA, Value IIIB, and Value IVC. Each of the other Model profiles through M also has the same attributes as Model Profile I, e.g. Attribute A, Attribute B . . . N, etc., but has a unique set of values. Although some individual model attribute values can be the same between two model profiles, the set of model attribute values in a model profile is unique. Also, some of the model profiles can have identical scores even though each has a unique set of model values.

Also, an attribute can include whether a patient has a particular characteristic or not, such as a particular disease. For example, if model Attribute A were gender, then the value in each profile associated with Attribute A would either be female or male. Accordingly, in a set of model profiles having multiple model profiles, some of the profiles can have the same value for the gender attribute. Also, some model attributes can have model values that correspond to a range. For example, if attribute B is weight, then the value in each model profile associated with Attribute B could be a range of weights, such as in 10 pound increments.

An adherence score can be assigned to a patient profile by matching the patient attributes and their associated attribute values in the patient profile with the model attributes and their associated model values in one of the model profiles. A patient profile can have more attributes than are used in a particular model. For example, a model can include only three attributes A, B, and C whereas a patient profile can have hundreds of attributes, including A, B, and C. Assigning an adherence score to a patient profile includes matching the values in the patient profile for attributes A, B, and C to the model values for attributes A, B, and C in one of the model profiles. The attribute values for Attributes A-C in the patient profile 110 shown in FIG. 1A match-up with the attribute values for Attributes A-C in Model Profile II in FIG. 1B. If the Model Profile II only had three attributes, including Attributes A-C then Patient Profile 110 would be assigned the same score as Model Score II because patient profile 110 has attribute values for Attributes A-C that match up with the unique set of attribute values in Model Profile II.

Adherence scores can be assigned to all the patient profiles in a patient population by matching patient attribute values in each of the patient profiles to the patient attribute values in one of the model profiles. Once one or more patient profiles have been assigned an adherence score, that score can be modified using a modifier into an adherence score for a particular use or application, such as for enhancing the accuracy of predicting patient adherence. Also, when multiple patient profiles have been assigned a score, various analyses can be performed, including grouping, indexing, and comparing.

Figure 2:
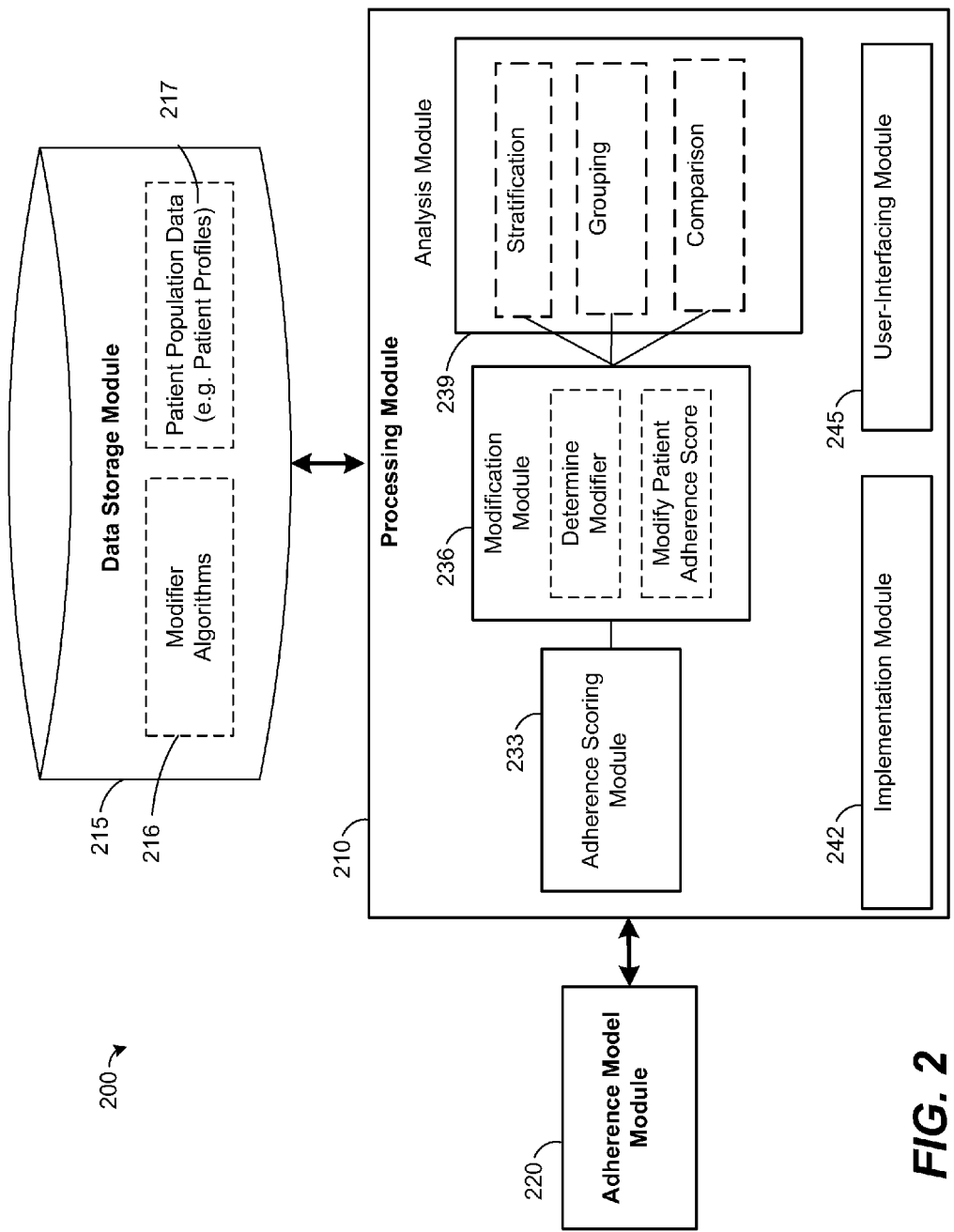
FIG. 2 shows an example system for assigning and modifying patient adherence scores.

FIG. 2 shows an example system 200 for assigning and modifying patient adherence scores. The system 200 includes processing module 210 which can be implemented using one or more data processing apparatuses, a data storage module 215 such as a data storage device, and an adherence model module 220. The adherence model module 220 can be located and run independent of the processing module 210. The data storage module 215 can store one or more modifier algorithms 216 and patient population data 217. Patient population data 217 can include patient profiles for various patients. Each of the profiles includes attribute data for the various patients.

The processing module 210 can include an adherence scoring module 233 for determining adherence scores, a modification module 236 for determining modifiers and for modifying the adherence scores, and an analysis module 239 for analyzing the results of the modified scores. The processing module can also include an implementation module 242 for implementing the results of the analysis module 239. For example, results of the analysis module can indicate interventions that can be implemented for a patient or patients to increase patient adherence. As discussed in more detail below, the implementation module can implement those interventions. The processing module 210 can also include a user-interfacing module 245 for interfacing with a user which can include providing data obtained from the various modules in the processing module 210 to the user.

The processing module 210 can obtain one or more patient profiles from the data storage module 215, such as patient profiles for a patient population, and provide the patient profiles to the adherence scoring module 233 where the patient profiles are assigned an adherence score. For example, the processing module 210 can obtain a patient adherence model from the adherence model module 220 for use by the adherence scoring module 233 to assign adherence scores to patient profiles. A patient adherence model can include an algorithm for determining an adherence score based on a specific set of patient attributes. Also, an adherence model can include, for example, a set of model profiles each profile having an associated model score. The adherence scoring module 233 can assign a score to the patient profile obtained from the data storage module 215 by matching the patient attributes and patient attribute values in the patient profile with the attributes and attribute values in one of the model profiles in the patient adherence model.

In some examples, the processing module 210 can provide a patient profile to the adherence model module 220 where an adherence score is determined. In such an example, the processing module 210 can provide a patient profile for a patient that includes only those attributes and attribute values necessary for the adherence model module 220 to assign an adherence score to the patient. Because a model uses a specific set of attributes as predictors for patient adherence, only those attributes and corresponding attribute values need to be sent to the adherence model module 220. This can be particularly important to maintain patient privacy if the adherence model module 220 is maintained by a third party.

Once a score has been determined for a patient profile, the score is provided to the modification module 236 where the score is modified using a modifier. The modifier can be determined by the modification module 210 based on a modifier algorithm 216 and patient data 217 stored in the data storage module 215. As will be discussed in more detail below, a modifier is used to modify an adherence score for a patient profile into a modified score for a particular application. For example, the model used to assign the adherence score can be a generic model for predicting adherence to any prescription.

A modifier can be used to modify the adherence score for a particular patient profile into a predictor for a specific application such as for a specific medication, for a specific class of medication, for a specific brand of medication, for a specific type of patient, for a specific disease, for a specific type of patient population, for an intervention, for a specific type of intervention, for a timing of intervention, etc. by adjusting the original patient adherence score. The same modifier algorithm can be used to determine modifiers for each of multiple patient profiles. The modifiers for each of the multiple patient profiles can be used to adjust the adherence scores obtained for each of the respective patient profiles.

In some examples, multiple modifier algorithms 216 can be obtained from the data storage module 215. The modification module 236 can use the multiple modifier algorithms 216 to obtain multiple modifiers for modifying an adherence score for a patient profile into a combination score for the patient. For example, a disease specific adherence modifier can be used to modify a score into a modified score for a specific disease. Likelihood of adherence can change based on a specific disease. For example, adherence can increase due to the serious nature of a disease, such as cancer. Other diseases, such as Alzheimer's, can decrease likelihood of adherence. Also, a specific disease in combination with other attributes can also affect likelihood of adherence. A second modifier, a cost modifier, for modifying an adherence score for cost of non-adherence can be obtained and used to further modify the score into a combination score indicating the likely cost of non-adherence of a patient with various diseases. In like manner, a combination score can be determined for each of multiple patients.

As described above, multiple patient profiles can be obtained from the data storage module 215 and assigned an adherence score. One or more modifiers can be applied to each of the multiple adherence scores to obtain a modified score for each of the multiple patient profiles. The analysis module 239 can stratify the multiple patient profiles based on the modified score for each patient profile. The analysis module 239 can group the patient profiles into groups based on the modified scores. Patient profiles having similar modified scores can be grouped together in a group. For example, patients with a high likelihood of not complying with a prescribed treatment can be grouped together. Grouping can also include grouping patients according to a particular attribute, such as patients who have the same value for an attribute can be grouped together. For example, patients from one medical plan can be grouped into one group whereas patients from another medical plan can be grouped into another group. As described in more detail below, the analysis module 239 can also compare modified scores of patients in one group with the patients in another group.

The implementation module 242 can implement intervention(s) to increase the likelihood of compliance with a prescription. For example, the implementation module 242 can implement an automated intervention such as an automated reminder email, phone call, text message, or mailing. In other examples, the implementation module 242 can send an automated reminder directly to the patient or to a nurse, a physician, a pharmacist, or the like to encourage the patient to adhere to their prescribed treatment. Also, incentive based intervention can be implemented to increase the likelihood of compliance. For example, a patient's co-pay for a drug can be decreased to encourage patient adherence. The implementation module can implement interventions using interactive voice response. For example, the implementation module 242 can automate follow-up phone calls to a patient during the prescription period to remind the patient to adhere to his or her medication and/or to ask whether the patient is adhering to his or her prescription.

The processing module 210 can determine an intervention modifier for a patient profile based on an intervention modifier algorithm. The modification module can use the modifier to modify an adherence score assigned to the patient profile into a modified score indicating the likelihood of a given intervention to increase the patient's adherence. The intervention modifier algorithm can also be used to determine intervention modifiers for each of multiple patient profiles. The intervention modifiers can be applied to the adherence scores obtained for each of those multiple patients respectively. The analysis module 239 can then group the patient profiles for the multiple patients into groups based on the modified scores. The implementation module 242 can then apply automated intervention to the group having the highest likelihood of increasing adherence as a result of intervention.

Because patients may respond differently to different interventions, multiple intervention modifier algorithms can be used to determine intervention modifiers for particular types of intervention. An adherence score for a particular patient profile modified with such an intervention modifier indicates the likelihood of the particular type intervention to increase patient adherence for the patient associated with the patient profile. The analysis module 239 can group the patient profiles for the multiple patients based on the modified scores for the specific intervention. This process can be repeated for multiple specific interventions to determine which patients will receive what specific type of intervention. In this manner, a specific intervention regime can be created for each patient in a patient population.

In some examples, a single intervention modifier algorithm can be used to group patients into groups for multiple interventions. For example, the intervention modifier algorithm can be used determine modifiers for each of multiple patient profiles. The modifiers for each of the multiple patient profiles can be used to modify the adherence scores assigned to each of the multiple patient profiles. The modified scores can indicate which intervention is most effective for each particular patient. The analysis module 239 can use the modified scores to group the patient profiles into groups for interventions that are likely to be effective for the patients in that group.

In some implementations, an intervention modifier can be combined in the modification module 236 with a cost modifier for determining the cost effectiveness of an intervention for a particular patient profile. For example, a cost modifier can be used to modify an adherence score into a modified score that indicates the costs attributed to non-adherence. A combination score is obtained by modifying the adherence score with both the intervention modifier and the cost modifier. This combination score indicates the cost effectiveness of intervention. Patient adherence scores for each of multiple patients can be modified with intervention modifiers and cost modifiers, and then grouped based on the cost effectiveness of intervention.

In some implementations, a budget can be received for implementing one or more intervention campaigns for a patient population. An intervention campaign can include rules regarding implementing one or more types of intervention, timing of intervention, and a group or groups of patients that should be targeted. Based on the budget and the cost of implementing the one or more types of intervention, an intervention campaign can be determined to most effectively alter patient adherence behavior of the population while staying within the budget. This can include grouping patients based on a modified adherence score. For example, a modified adherence score can indicate likelihood of non-adherence and disease severity. Patients in the population with a low likelihood of adherence and a relatively high disease severity can have a relatively low modified score and can be grouped into a group for a more intensive and more expensive intervention regime, such as high-frequency, direct contact, whereas patients with higher likelihood of adherence and lower disease severity can have relatively higher modified scores and can be targeted with a less expensive form of intervention (e.g. less direct and less frequent) such as via e-mail, facsimile, text message, or automated phone calls.

As mentioned above, the timing of intervention can be determined for the members of the group based on a modified adherence score. Timing can include frequency, or can be based on a schedule such as dosing schedule and/or a refill schedule. The frequency of intervention can be tailored to a dosing schedule of a particular prescription such as a once per day intervention for a daily dosing schedule versus once per month intervention for a once per month dosing schedule. For example, the dosing regimen for medications to treat or prevent osteoporosis can be once daily, to weekly, to monthly, to annual dosing for treatment or prevention of osteoporosis. Also, intervention can be timed according to a refill schedule. For example, for patients with poor adherence to medications due to not being able to get to a pharmacy may benefit from receiving 90 days worth of medication through a mail delivery option versus going to a pharmacy every 30 days.

The following attributes in a patient profile can help determine the timing of an intervention: formulary design, copay, drug benefit, disease status, number and types of comorbidities, medication profile in terms of side effects or efficacy or therapeutic effect (perceived or not perceived). For example, if a patient in a patient population has a low modified adherence score and is known to be more sensitive to medication costs (i.e., through survey or specific patient attributes) then the patient could be referred to receive more coupons (frequency or value of the coupon) or receive coupons sooner than other patients with higher modified adherence scores. Coupons can also be defined as any financial incentives (or disincentives) to encourage medication adherence (e.g. rewards or point card programs). In some examples, if a patient in a patient population has a low modified adherence score and their medication treatment option has known side effects that lead to patient non-adherence, then the timing of the intervention could be made as soon as the prescribing of that particular medication. The intervention could include, for example, greater education and counseling on awareness and how to manage possible side effects. The timing would be performed as soon as possible (i.e. close to time of prescribing) in order to avoid medication non-adherence once side effects arise.

If a patient is more aware of the symptomatic relief that is expected with a medication, then the greater the likelihood that the patient is to be adherent. For example, a patient that is taking a medication to treat high cholesterol may take a type of medication referred to as a statin which can have no effect on the symptoms perceived by the patient. If a patient does not understand that the effect of the medication is seen through monitoring his or her blood then this patient is can have a higher likelihood of discontinuing therapy (be non-adherent) because of falsely concluding that the medication is not working. In such an example, a patient with a low modified adherence score can be aligned with a more timely intervention (e.g., sooner within initiation of therapy) that addresses their understanding of how their medications work.

The user-interfacing module 245, allows a user to access the data produced by each of the modules in the processing module 210 and to adjust various settings for the processing module. A user can access the adherence scoring module 233 to see the results of assigning adherence scores to one or more patient profiles. The user can also access the modification module 236 to see the results of the modification. The user can also access the analysis module 239 to see the analysis results. For example, a physician can access the analysis module to view a comparison of a patient's adherence with other patients in a population. A user can also adjust and/or update the algorithms used to analyze the data provided by the modification module 236. A user can also access, from the implementation module, statistics such as how many and what kind of interventions were implemented. Also, a user can use the user-interfacing module 245 to access and adjust the modifier algorithms and patient data in the data storage module 215.

Figure 3:
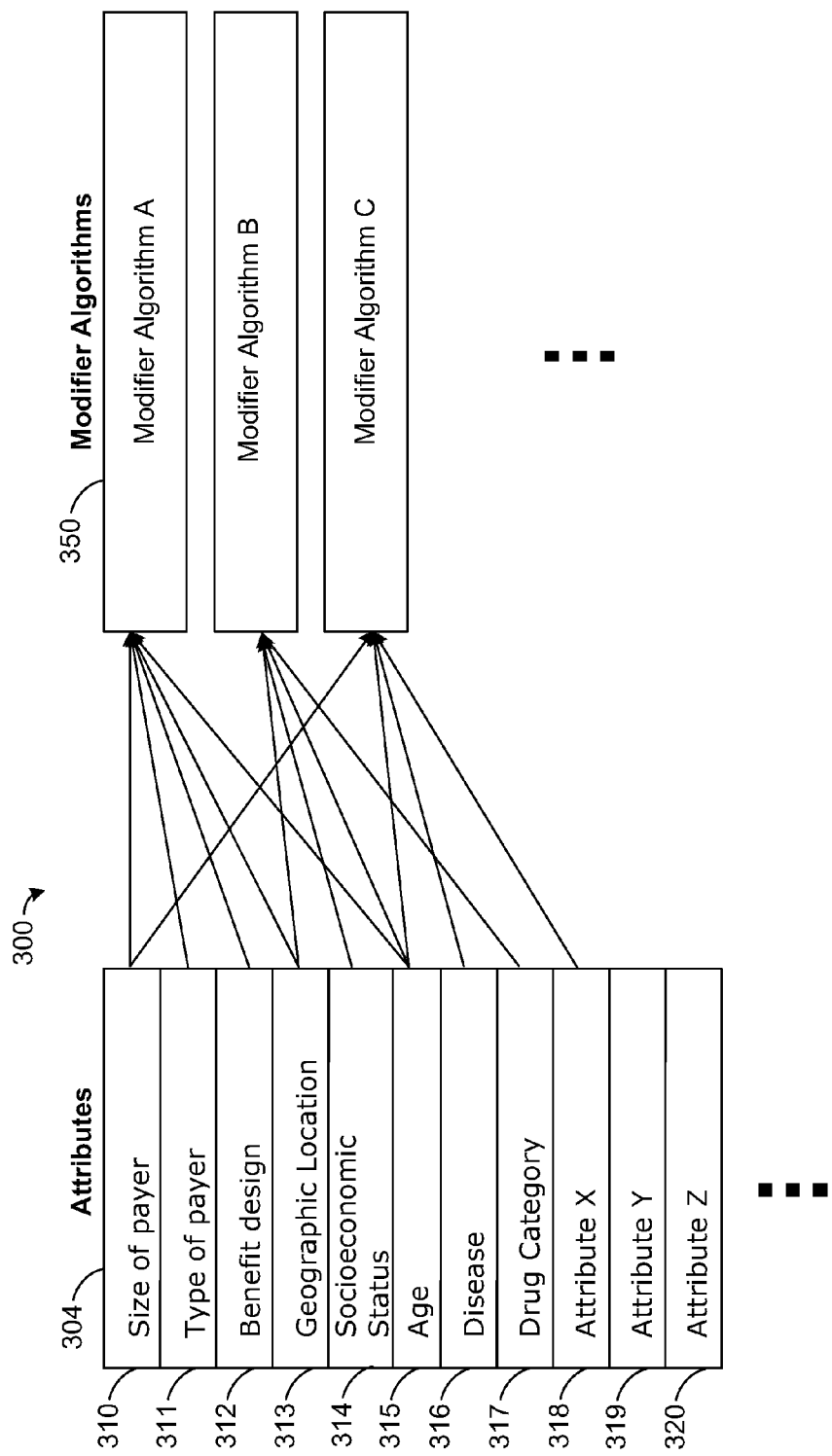
FIG. 3 shows an example list of modifier algorithms and attributes associated with the modifier algorithms.

FIG. 3 shows an example list of modifier algorithms and attributes associated with the modifier algorithms. A column 304 shows an exemplary list of various attributes that can be included in a patient profile, including size of payer 310, type of payer 311, benefit design 312, geographic location 313, socioeconomic status 314, age 315, disease 316, drug category 317, and other attributes 318-320 which indicate other attributes X-Z respectively.

Each modifier algorithm in column 350 includes weights for various attributes depending on the particular application the modifier algorithm is designed for. For example, Modifier Algorithm A shown at 350 includes weights for Size of Payer 310, Type of Payer 311, Benefit Design 312, Geographic Location 313, and Age 315. Modifier Algorithm B includes weights for Geographic Location 313, Age 315, and Drug Category 317. Modifier Algorithm C includes weights for size of payer 310, age 315, disease 316 and attribute X shown at 317. The modifier algorithms shown in column 350 can include any number of modifier algorithms. The attributes can include any number of attributes. Each modifier algorithm can have weights for any number of the attributes in column 304.

A modifier algorithm can include weights for one or more of the attributes that were used in the model to determine an adherence score. In some examples, the modifier algorithm can include weights for attributes different from the attributes used in the model to determine the adherence score. For example, as shown in FIG. 1B, the model 150 uses attributes 1 ... N as predictors for adherence. A modifier algorithm can include weights for one or more attributes that are not included in the attributes 1 ... N.

Figure 4:
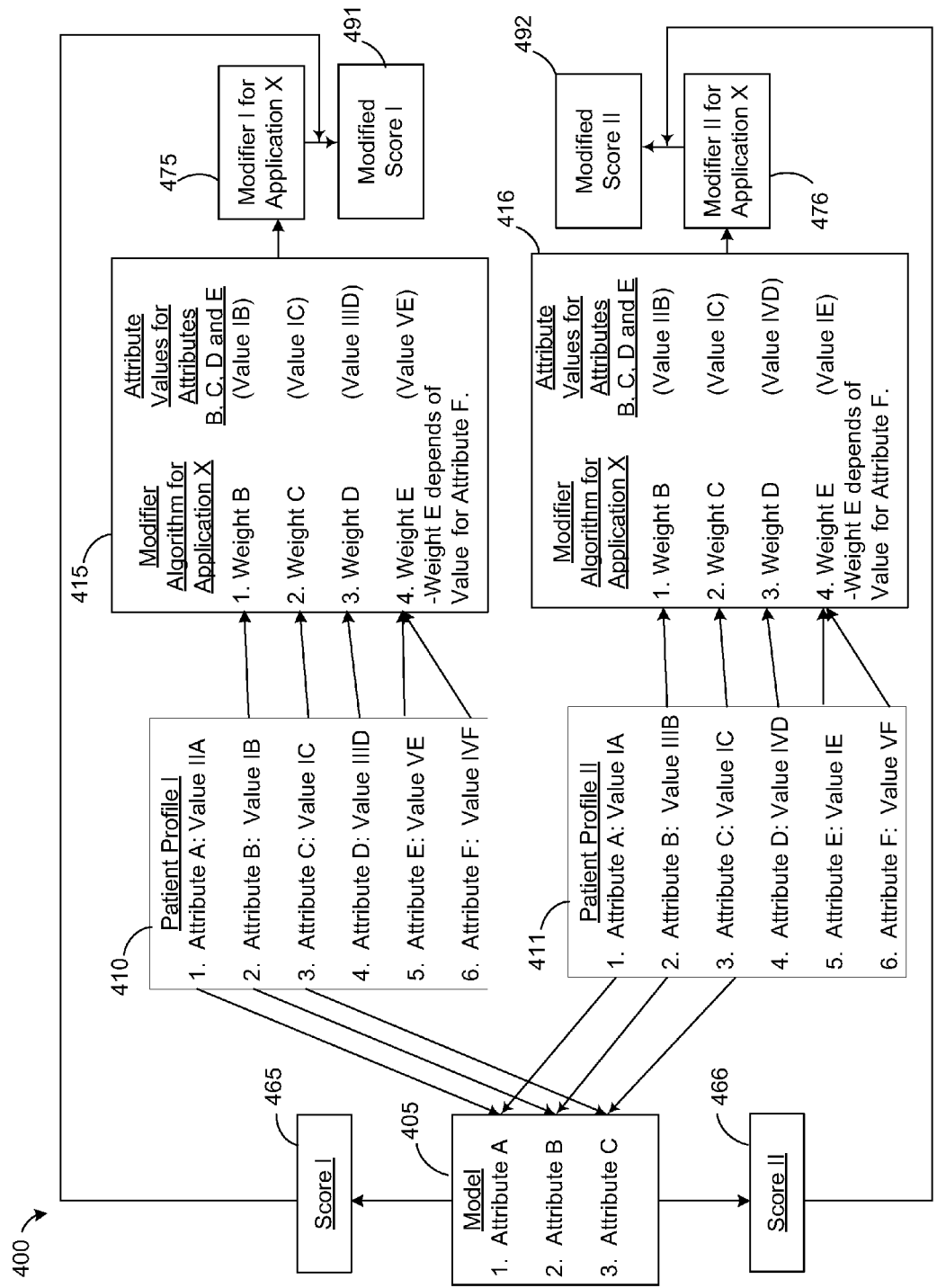
FIG. 4 shows an example of determining adherence scores and modifiers.

FIG. 4 shows an example of determining adherence scores and modifiers. This example involves a model 405, a patient profile 410, a patient profile 411, and a modifier algorithm for application X shown at 415 and 416. Both Patient Profile I shown at 410 and Patient Profile II shown at 411 have a list of attributes A-F, each attribute having a patient attribute value. The Patient Profile I has the following attributes and values: Attribute A has a value IIA; Attribute B has a value IB; Attribute C has a value IC; Attribute D has a Value IIID; Attribute E has a Value VE; and Attribute F has a Value IVF. Attributes A, B and C in the patient profile 410 match up with the attributes in the model 405. A patient adherence score can be obtained from the model 405 based on a specific set of attributes, which in this example include Attributes A, B, and C. Accordingly, Patient Profile I shown at 410 can be assigned a patient adherence Score I shown at 465 based on the values of Attributes A, B, and C in the patient profile I. Patient profile II shown at 411 is assigned a Score II shown at 466 based on the values of Attributes A, B, and C in the patient profile II shown at 411.

Modifier Algorithm for Application X is used to determine a modifier for one or more patient profiles for a particular application X. Modifier algorithm for application X has weights B, C, D, and E associated with attributes B, C, D, and E respectively for weighting the values associated with attributes B, C, D, and E for a particular patient profile. For example, a Modifier I shown at 475 can be determined for Patient Profile I using Modifier Algorithm for Application X. To do so, Weight B is applied to Value IB, Weight C is applied to Value IC, and Weight D is applied to Value IIID, and Weight E is applied to Value VE. Weight E, however, depends on the value associated with Attribute F, which in the patient profile 410 is Value IVF. The combination of weighted attribute values shown at 415 determines Modifier I for Application X. Modifier I can be used to modify Score I assigned to Patient Profile Ito determine a modified score (Modified Score I) for Application X shown at 491.

A modifier can also be determined for Patient Profile II using the same Modifier Algorithm for Application X. At 416, Modifier Algorithm for Application X is used to determine a modifier II shown at 476 for Patient Profile II. To do so, Weight B is applied to Value IIIB, Weight C is applied to Value IC, and Weight D is applied to Value IVD, and Weight E is applied to Value IE. Weight E, however, depends on the value associated with Attribute F, which in the patient profile 410 is Value VF. The combination of weighted attribute values shown at 416 determines Modifier II for Application X. Modifier II can be used to modify Score II assigned to Patient Profile II to determine a modified score (Modified Score II) for Application X shown at 492.

A modifier algorithm can include weights for various attributes depending on the application. In some examples, a modifier algorithm can include weights for various attributes for determining a modifier for a specific application. The modifier can be used to modify an adherence score into an enhanced adherence score (e.g., for a specific disease, for a specific patient population etc.), a cost score, a risk score, an intervention score, or a score for clinical trial completion. For example, a general adherence score can be assigned to a patient profile using only a specific set of attributes, such as demographic attributes. The general adherence score can be modified into a more predictive adherence score by applying a modifier which was determined based on attributes in the patient profile that were not used to assign the original adherence score. For example, the general adherence score can be modified into an adherence score for a particular disease by applying a modifier that was determined based on attributes associated with the disease. As will be discussed in more detail below, weights for particular attributes in a modifier algorithm such as for attributes associated with a disease can be dependent on the value of other attributes such as age, weight, ethnicity, gender etc. A similar result can be obtained by adjusting a weight applied to attributes such as age, weight, ethnicity, and gender, based on the value of another attribute such as disease.

Various attributes can be predictors for various applications, including adherence, cost, risk, and intervention. The type of payer ((e.g., Managed Care Organization, Third Party Administrator, Self-Insured, CMS, Military, etc.) can be a predictor for adherence because payer type can be driven by the characteristics of the membership. For example, members of a particular medical plan can have a lower socioeconomic status which can reduce the entire adherence score for this population by a specific amount. Type of payer can be a predictor for various applications because some organizations can have different lines of business (commercial HMO versus PPO products).

Depending on the particular application, a modifier can be based on overall drug benefit, e.g. a combination of all benefit design characteristics. For example, depending upon the drug benefit, there can be various deductibles, co-pays, and caps, which can drive adherence behavior for financial reasons. For example, some medical plans (e.g. Medicare) can have a "donut hole" (i.e. the medical plan pays for treatment up to a lower threshold and stops providing payment until an upper threshold is met). In this example, when the lower threshold is met, a lower income patient is more likely to opt to either stop taking expensive medications, or change to a generic or therapeutic alternative, if available.

A modifier can be based on formulary design. Formulary design can include various restrictions such as open formulary and closed formulary. Formulary design can also include the drugs or drug classes a medical benefit will and will not pay for. Formulary design can also include tiers of drugs and the amount of co-pay for each tier. These, in effect, can drive the relative co-pay amount for a drug or a class of drugs as compared to other drugs or other drug classes. Patient behavior such as adherence behavior can also be driven by formulary design.

Prior authorization requirements can also be a predictor for adherence. Prior authorization can introduce hurdles for a patient and/or physician to prescribe and obtain a medication. These hurdles introduce a greater likelihood for poorer persistence and for non-adherence. A modifier can be based on step therapy rules. According to some therapy rules, if a drug is requested, the patient may need to try and fail (e.g. have adverse side effects, show ineffectiveness of drug etc.) another drug first before the requested drug is granted access. If only the requested drug is desired, a higher co-pay is assessed to the patient. Both prior authorization requirements and step therapy rules can drive patient behavior such as which drugs they buy and a patient's adherence to a drug prescription.

Benefit design attributes such as co-payment, cost of drug, availability of generic drugs, and availability of therapeutic alternatives can each individually affect patient behavior depending on the application. Increase in cost of drug or increase in co-payment can increase non-adherence. In some instances, a modifier algorithm that includes weights for these attributes can be affected by the value of other attributes. For example, a weight for co-payment or cost of drug in an modifier algorithm for enhanced adherence prediction can be affected by the value of the socioeconomic status attribute because non-adherence among lower income patients can increase more as a result of increase in cost than among higher income patients. Also, availability of generic drugs, and availability of therapeutic alternatives can also affect adherence. Adherence behavior for high income patients is usually not affected as much by these attributes as are low-income patients.

Age can be also predictor for adherence. In some examples, adherence prediction for a given disease and for a given medication can vary based upon gender and/or ethnicity. Also, the cost and/or risk for some diseases can vary depending on age, gender, and ethnicity. Age and gender can also be predictors for intervention. For example, some age groups respond differently to different types of communication such as email, letters, text messages, phone calls, direct contact from a health care profession etc. In like manner, from a specific geographic location of a patient (e.g. zip+4), other characteristics can be inferred, including socioeconomic status, purchasing patterns, ethnicity, and other demographics that, when combined with other attributes, can predict adherence behavior, cost, risk, and even how a patient will respond to an intervention. Also, particular patients in a geographic market with high layoffs may have a greater propensity for non-adherence.

As discussed above, socioeconomic status (income, education, occupation) can be predictors of adherence in many applications. A modifier algorithm that includes a weight for socioeconomic status can be based on the value of other attributes such as drug benefit design. In like manner, the weight for other attributes can be based on the attribute value of socioeconomic status. Socioeconomic status can also be a predictor for risk. For example, patients in a low socioeconomic status can have less access to or be more reluctant to access high quality medical treatment and therefore have an increase in risk. Also, socioeconomic status, for example, can be a predictor for eating habits and therefore also be a predictor for risk of certain types of diet-related medical conditions. Also, education level can indicate the degree a patient will understand a disease, a drug, and how to take the drug, which can influence adherence behavior. A weight for education level can also be based on other attributes that indicate the simplicity or complexity of a drug treatment, such as prescription complexity, therapy rules, etc.

A modifier can be based on other patient attributes as well. For example, recreational drug/alcohol use, patient beliefs about the disease or treatment, and confidence in the physician can be used to enhance adherence prediction. Recreational drug and alcohol use can also be a predictor for cost and risk, especially for some medical conditions. Accordingly, a weight for a medical condition in a modifier for risk or cost can depend on the value of the recreational drug and alcohol use attribute. Patient beliefs can also be predictors for intervention. For example, if non-adherence is strongly influenced by a particular belief, then intervention can be adjusted to focus on educating patients with that belief. Whether a patient has social support can also affect adherence. In certain populations (e.g., children, elderly, certain diseases), social support can impact adherence. Therefore, weights applied to age or disease can be based on whether social support is available. Motivation to be medication adherent and perceived control of and responsibility for medication adherence can be predictors of adherence at the ends of the age spectrum (the very young and the very old).

A modifier can be based on disease, disease severity, and co-morbidities. Disease, disease severity, and co-morbidities can be predictors of adherence, risk, and cost. Depending on the application, a modifier algorithm can have weights for disease attributes. For example, some diseases, because of the serious nature of the disease (e.g., cancer), are associated with a higher adherence rate. Other diseases, because of the disease itself (e.g. Alzheimer's, schizophrenia, psychiatric disorders), can be associated with a lower adherence rates. Some diseases, because drug treatment brings symptomatic relief (e.g. rheumatoid arthritis), can be associated with higher adherence rates. Some diseases are associated with other diseases as they become more severe (e.g., diabetes) which leads to increased complexity of care as well as sequelae (decrease visual acuity) which can be associated with decreased adherence rates. Also, some diseases can be affected by attributes such as a patient's weight. For example, the heavier a patient, the greater the risk that can be associated with some diseases (e.g. diabetes) based on patient's weight. Also, certain diseases can be more serious among various ethnicities, genders, and ages. Accordingly, in a risk modifier algorithm the value of a weight for a disease attribute can also be based on ethnicity, gender, and/or age. Time with a disease or a condition can also affect adherence behavior. In certain instances, the longer a patient has a condition, the less likely the patient is to be compliant with a prescription.

A modifier can also be based on drug related attributes. For example, some drug categories, because of disease treated, side effect profile, and other factors, can have a lower adherence rate. Prescription complexity, such as the number of concurrent drugs and the number of different dosing schedules, can be associated with lower adherence. A modifier algorithm that includes a weight for prescription complexity can be based on the value of other attributes such as education, age, etc.

A modifier can also be based on pharmacy related attributes. For example, patients obtaining their medications from independent pharmacies are more likely to refill their medications. Location to pharmacy can be a predictor of level of access to care. Access to care can affect cost of treatment, likelihood of adherence, and for some diseases can affect risk. For some medical conditions, patients residing near specialty pharmacies may be more likely to adhere than being farther from a specialty pharmacy, depending upon the services provided. Pharmacies that provide additional counseling or services like vaccinations will have better patient adherence. Also, modifiers can be based on attributes related to a patient's physician. Physicians with a specialty background often see patients who have a greater level of severity for a specific condition or greater co-morbidity, which in turn can affect adherence rate. Access to specialist in remote, rural areas has been shown to drive differences in medical resource utilization, which in turn can affect overall cost of treatment, adherence, and even risk for certain diseases.

Figure 5:
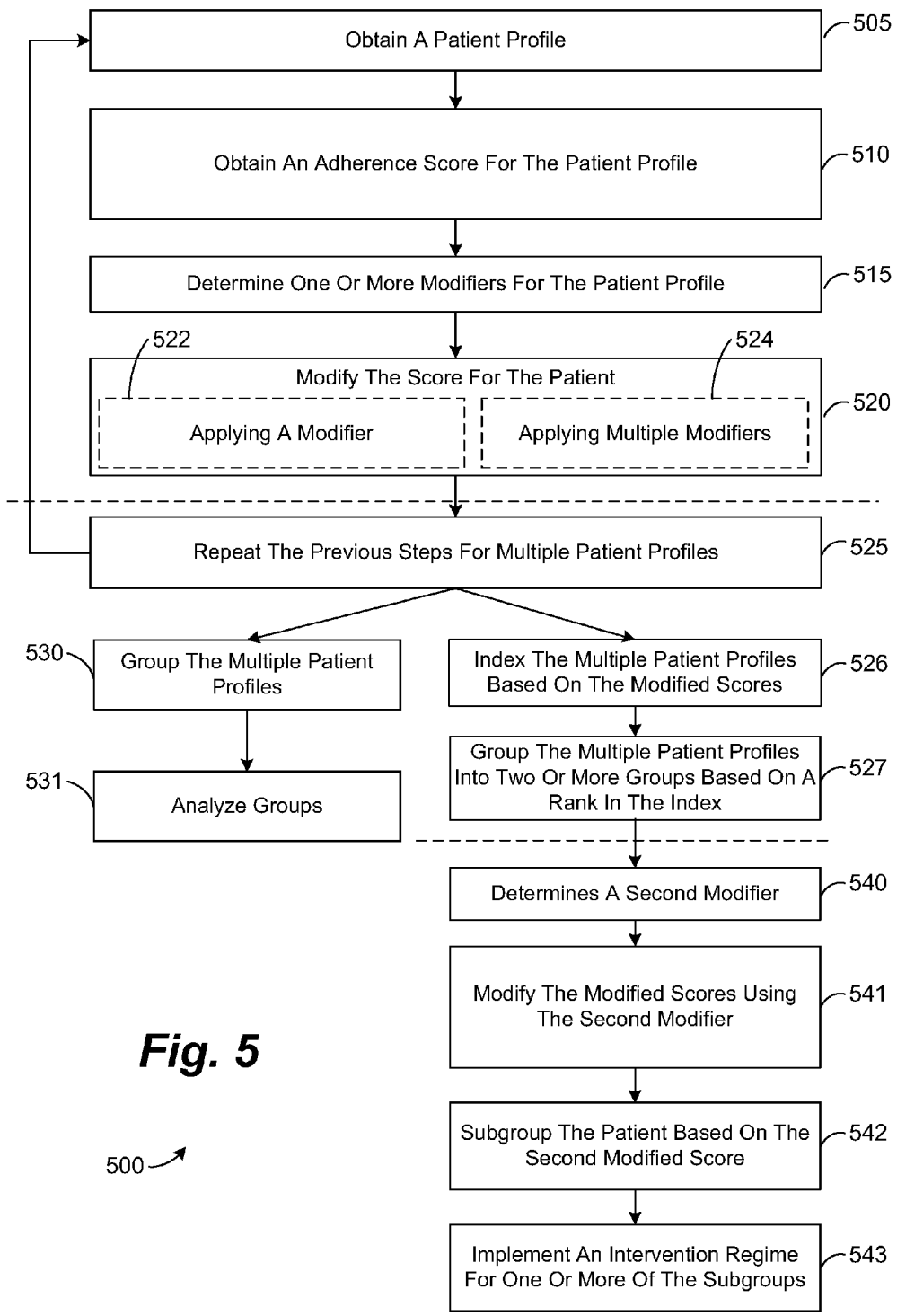
FIG. 5 shows an example process for modifying adherence scores and for using modified scores.

FIG. 5 shows an example process 500 for modifying adherence scores and for using modified scores. At 505, the process 500 obtains a patient profile, e.g. from a data storage device. The patient profile includes multiple patient attributes and each patient attribute including a value. At 510, the process 500 obtains an adherence score for the patient profile. For example, an adherence model can be used to determine an adherence score based on various attributes. In some examples, the patient profile or select attributes and attribute values from the patient profile are provided to an adherence model module for generating an adherence score using a model. In some examples, the adherences score can be obtained using a patient scoring module to assign an adherence score. The adherence score can be obtained by matching values of attributes in the patient profile to the values of attributes in a model profile from as set of model profiles. In some examples, a patient adherence score associated with the patient profile can be stored in a data storage device. The process 500 can obtain the patient adherence score from the data storage device.

At 515, the process 500 determines one or more modifiers for the patient profile. The modifiers are each for modifying an adherence score into a modified score for a particular application. A modifier can be determined using a modifier algorithm that includes a set of weights for weighting attribute values associated with a set of attributes. At 520, the process 500 modifies the adherence score into a modified score for a particular application. Optionally, the process can modify the adherence score by applying a modifier at 522 or can also optionally modify the adherence score applying multiple modifiers at 524. For example, at 524, the patient adherence score can be modified by applying a cost modifier and a risk modifier. Cost indicates the cost of non-adherence. Risk can include, for example, the likelihood of hospitalization, the likelihood of an emergency room visit, the likelihood of morbidity, and the likelihood of contracting other medical conditions as a result of non-adherence. In this manner, two modifiers for a patient profile can be used to modify the adherence score for the patient profile into a modified score indicating the combination of cost and risk of non-adherence.

Also at 525, the previous steps (505, 510, 515, 520) can optionally be repeated for a second or more patients. A patient profile can be obtained 505 for the second or more patients. An adherence score can also be obtained 510 for each of the second or more patient profiles. One or more modifiers can be determined 515 for the second or more patients. In this manner, a modified score for a particular application can be obtained for all of the patients in a patient population. For example, the adherence score for each of the multiple profiles can be modified using both cost and risk modifiers as discussed above.

The modified scores for the second or more patients can be used for various analyses. For example at 526, the multiple profiles can be indexed based on the modified scores. Continuing with the risk-cost example, at 526 the multiple patients can be indexed based on their modified scores by ranking them from lowest risk-cost to highest risk-cost. At 527, the multiple patients can be grouped into two or more groups based on their rank in the index, such as a group for top 20% based on risk-cost, a group for the lowest 20% based on risk-cost, and so forth.

Optionally at 540, the process determines a second modifier for each of the first and second or more patient profiles. At 541, the process 500 modifies the modified scores for the patient profiles in one of the groups using the second modifier into a second modified score for a second application. For example, the second modifier can be determined using an intervention modifier algorithm that includes a set of weights for attributes that are predictive of the effectiveness of an intervention. The intervention algorithm can be used to determine a modifier for each of the patient profiles grouped in the top 20% based on cost and risk. The intervention modifier for each of the patient profiles grouped in the top 20% can be applied to the modified adherence scores for each of the patient profiles grouped in the top 20%.

At 542, each of the multiple patient profiles is sub-grouped based on the second modified score. For example, if the second modified scores for the patient profiles in the top 20 percent were modified using an intervention modifiers, each of the patient profiles can be sub-grouped into sub-groups based on which intervention is most likely to increase adherence for the patient associated with each of the profiles. For example some of the patients may be more likely to increase adherence based on an email reminder and those patients can be grouped together, while others may be more likely to respond to an economic incentive, and those patients can be grouped together. At 543, an implementation regime can be implemented for one or more of the sub-groups based on the intervention that is most likely to increase the adherence scores for the patients in those sub-groups. In this manner, the most effective intervention regimes can be used to target patients in a population that are most likely to have an increase in cost due to non-adherence using intervention regimes that are most likely to increase adherence amongst those patients.

The modified scores obtained at 525 for the second or more patients can be used for other analyses. For example at 530, the multiple patient profiles can be grouped based on a common value for a particular patient attribute. For example, the patient profiles can be grouped based on medical plan, group, or provider. At 531, the groups can be analyzed. For example, the overall scores (e.g. the average or the mean of all of the scores) for each of the plans can be compared for benchmarking, for decreasing costs for particular plans, for decreasing risk, etc. For example, if risk and cost modifiers were used to modify the adherence scores for multiple patient profiles from multiple medical plans then each of the multiple profiles can be grouped based on medical plan. In this manner, the cost and risk of each of the medical planes can be compared based on the average cost-risk of those medical plans. Benchmarking can include comparing the likely performance of various plans, such as profitability or success rate of a prescribed treatment.

Figure 6:
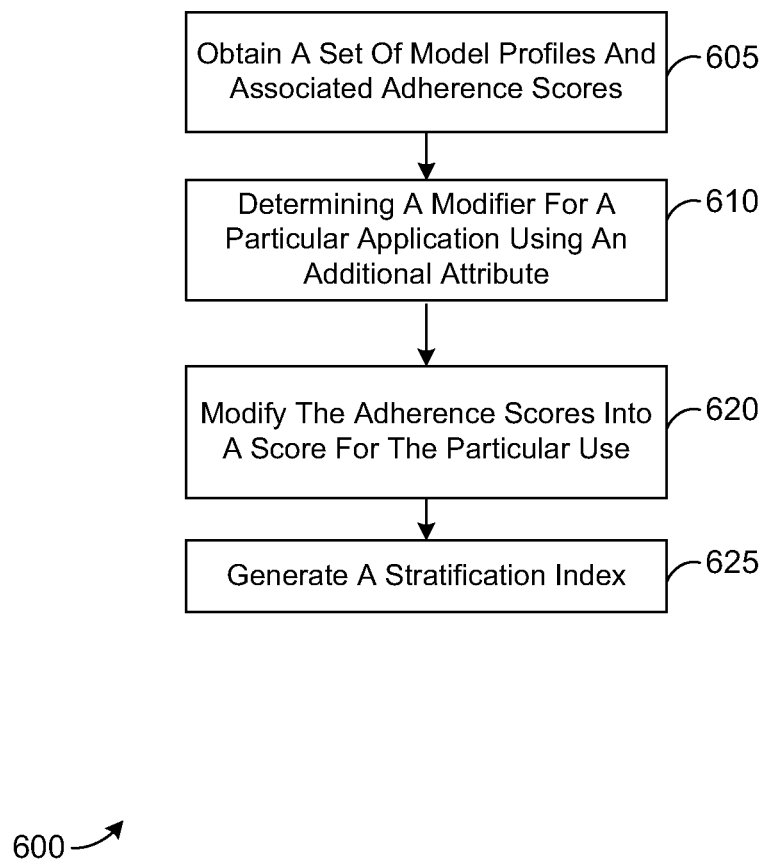
FIG. 6 shows an exemplary process for modifying adherence scores associated with multiple model profiles.

FIG. 6 shows an exemplary process 600 for modifying adherence scores associated with multiple model profiles. At 605, process 600 obtains a set of model profiles. Each model profile has a set of attributes and each attribute has a value. Each of the model profiles also has an associated model score that indicates likelihood of adherence of a patient having attributes with the same values as the model profile. At 610, the process 600 determines an application-specific modifier for modifying the score of each of the model profiles based on one or more additional attributes different from the attributes in the model profile. Each of the additional attributes has a value. For example, a modifier algorithm can include a weight that can be applied to one of the additional attributes and the modifier can be a function of one of the attributes in the original model profile. In one such example, each of the model profiles has socioeconomic status as one of the model attributes. The additional attribute can include a drug plan. A single attribute value, e.g. a particular medical plan, for the additional attribute is used to determine the modifier for each of the model scores. The co-pay structure for that particular medical plan can impact patient adherence behavior based on socioeconomic status. A weight can be applied to the value of the additional attribute based in part on the value of the socioeconomic status attribute. For example, if the particular medical plan has a high co-pay structure, the adherence score among profiles indicating a low-income will decrease. In this manner, the model score can be adjusted based on income in accordance with a particular medical plan. At 620 the process modifies each of the adherence scores into a modified score for the particular application. At 625, the model profiles can be indexed based on the modified scores.

Figure 7:
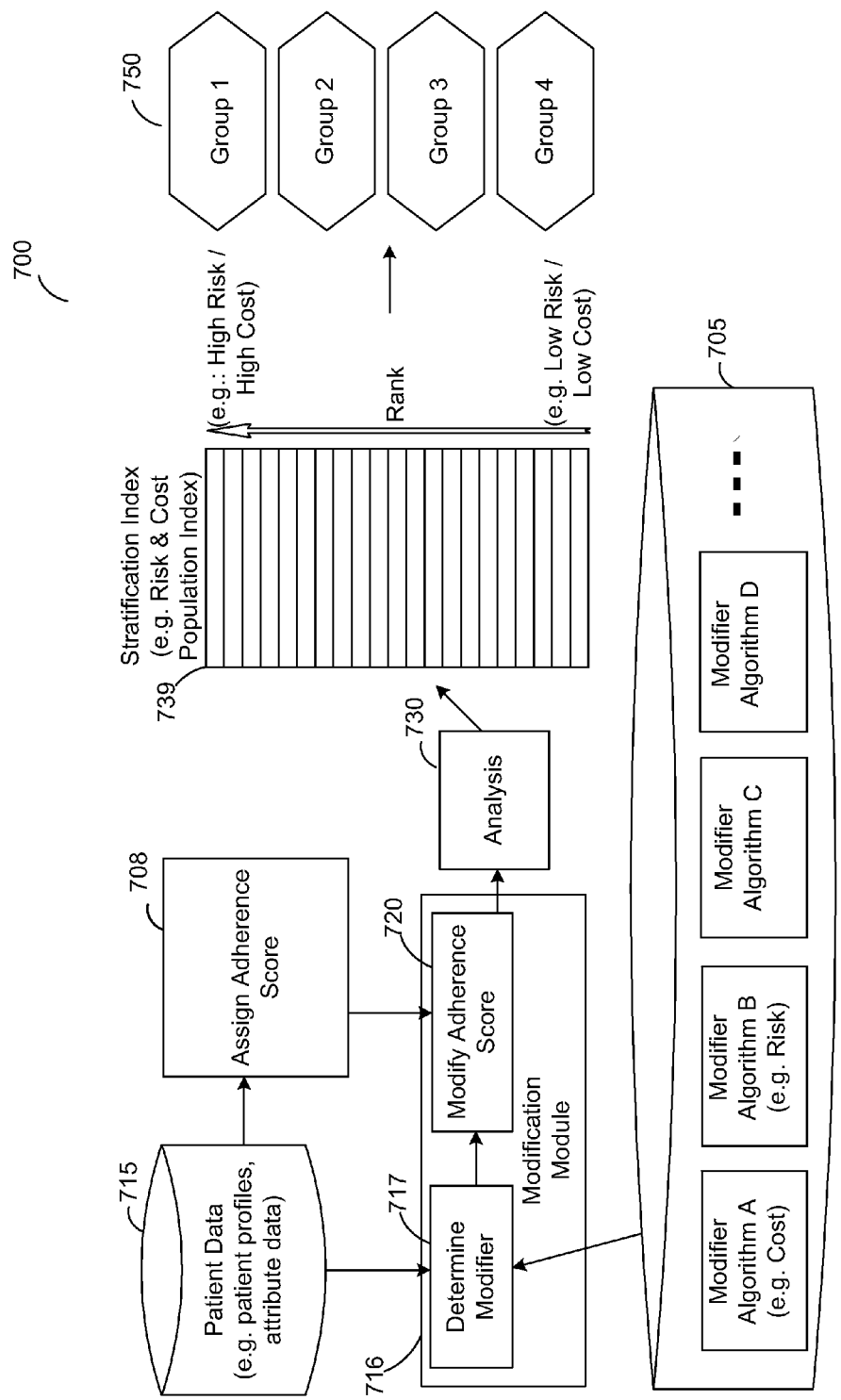
FIG. 7 shows an example of modifying patient adherence scores.

FIG. 7 shows an example of modifying patient adherence scores. A data storage 705 device stores one or more modifier algorithms. A second data storage device 715 can also be used to store population data including patient profiles for multiple patients. In some examples, the modifier algorithms can be stored in the same storage device as the population data. A patient profile can be supplied to e.g. a modification module 716 where at 717 a modifier is determined for the patient profile using a modifier algorithm, such as Modifier Algorithm A from the data storage device 705. The same patient profile from the data storage device 715 can be assigned a patient adherence score at 708, for example by an adherence scoring module, and also supplied to e.g. a modification module 716 where at 720 the adherence score is modified using the modifier determined at 717. In this manner, a modified adherence score can also be determined for multiple patient profiles stored in the data storage device 715 using the same modifier algorithm from the data storage device 705, e.g. Modifier Algorithm A.

In some examples, a second or more modifier algorithms can also be obtained from the data storage device 705. The second or more modifiers algorithms can be used to determine a second or more modifiers for a patient profile at 717. Using the second or more modifiers, a combination score can be determined at 720 by adjusting the adherence score using the multiple modifiers determined at 717. In similar manner, a combination score can also be determined for multiple patient profiles stored in the data storage device 715 using the modifier, e.g. using Algorithms A and Algorithm B.

The modified scores and the patient profiles are supplied to an analysis module 730 where the patient profiles are indexed based on their respective modified scores and grouped into multiple groups. A graphical representation of an index 739 shows the patient profiles ranked from lowest to highest based on the modified score. Another graphical representation 750 shows the patient profiles grouped into four groups. They can be grouped according to a rank in the index. In some examples, the patient profiles can be grouped based another attribute such as medical condition, medical plan etc.

For example, according to the diagram 700, multiple patients having the same disease (e.g. diabetes) can be stratified according to risk. The patient profiles for multiple patients having the same disease are provided from the data storage device 715 to e.g. an adherence scoring module 708 where each of the patient profiles is assigned an adherence score. A risk modifier for each of the patient profiles is determined at 717 using a risk modifier algorithm, e.g. Modifier Algorithm B. The adherence score for each of the patient profiles is modified using each of the respective risk modifiers for each of the patient profiles into a risk score indicating the likelihood of a serious condition related to the disease (e.g. morbidity/mortality risk). The analysis module 730 can then index the patient profiles from lowest risk to highest risk and can group them into groups based on risk by placing the highest risk patients in Group 1 and the next highest risk patients in Group 2 etc. The analysis module can also group them according to another attribute such as medical plan to compare the risk of non-adherence for a particular disease between medical plans.

Also, multiple patients having the same disease (e.g. diabetes) can be stratified according to cost. The patient profiles for multiple patients having the same disease are provided from the data storage device 715 to an adherence scoring module 708 where each of the patient profiles is assigned an adherence score. A cost modifier for each of the patient profiles is determined at 717 using a cost modifier algorithm, e.g. Modifier Algorithm A. The adherence score for each of the patient profiles is modified using each of the respective cost modifiers into a cost score indicating the likely cost of treating a patient (e.g. over the course of the next year). The adherence scores and the patient profiles are supplied to the analysis module 730 for further analysis. In some examples, where patient specific data is not necessary for the analysis, just the scores and the number of patients at each score can be supplied to the analysis module. In other examples, where not all patient profile data is necessary, sufficient data to associate the scores with a patient can (e.g. using a patient identifier) can be sent to the analysis module. The analysis module 730 can then index the patient profiles from lowest cost to highest cost and can group them into groups based on cost by placing the highest cost patients in Group 1 and the next highest cost patients in Group 2 etc. Also, the patient profiles can be grouped according to medical plan for comparing the cost for each medical plan.

Further, multiple patients having the same disease (e.g. diabetes) can be stratified according to both cost and risk. The patient profiles for multiple patients having the same disease are provided from the data storage device 715 to e.g. an adherence scoring module, where at 708 each of the patient profiles is assigned an adherence score. A cost modifier and a risk modifier for each of the patient profiles is determined at 717 using e.g. Modifier Algorithm A for cost and Modifier Algorithm B for risk. The adherence score for each of the patient profiles is modified using the respective cost modifiers and the respective risk modifiers into a cost-risk combination score indicating the likelihood of a severe and costly condition associated with the disease. The analysis module 730 can then index the patient profiles based cost from lowest cost-risk to highest cost-risk and can group them into groups based on cost and risk by placing the highest cost patients in Group 1 and the next highest cost patients in Group 2 etc. The patients in Group 1 can be provided to an implementation module as shown in FIG. 1, for implementing an intervention such as a disease management program to decrease the likelihood of a severe condition.

Grouping in this manner can be helpful for various reasons including comparing, ranking and/or benchmarking For example, in order to price medical coverage in a medical plan for a disease, it can be useful to compare the cost and/or risk of patients with the disease to patient profiles of one or more patient populations having a different medical condition (e.g. one population having hypertension, one population having asthma, etc.) To compare the potential cost and risk of the disease with the potential cost and risk of other conditions, cost modifiers and a risk modifiers can determined for and applied to patient profiles of the multiple populations including the patient profiles of patients with the disease in order to obtain a combination risk-cost score for each of the patient profiles. The analysis module 730 then indexes the patient profiles into an index 739 from lowest to highest. The patient profiles are then grouped based on medical condition such as patient profiles having the disease being evaluated in Group 1, patient profiles in a population having another condition in Group 2, patient profiles in a population having a third condition in Group 3 etc. An overall score for each of the different disease groups can be calculated (e.g. median or mean score etc.) and compared. In this manner, the cost-risk score of providing insurance coverage for the disease can be ranked against the cost and risk of providing insurance coverage for other diseases. Ranking the cost and risk of covering a particular disease can help in setting effective and competitive insurance premiums. In like manner, the overall cost-risk score of an existing medical plan can be benchmarked against other existing medical plans to determine if, for example, premiums need to be adjusted.

Figure 8:
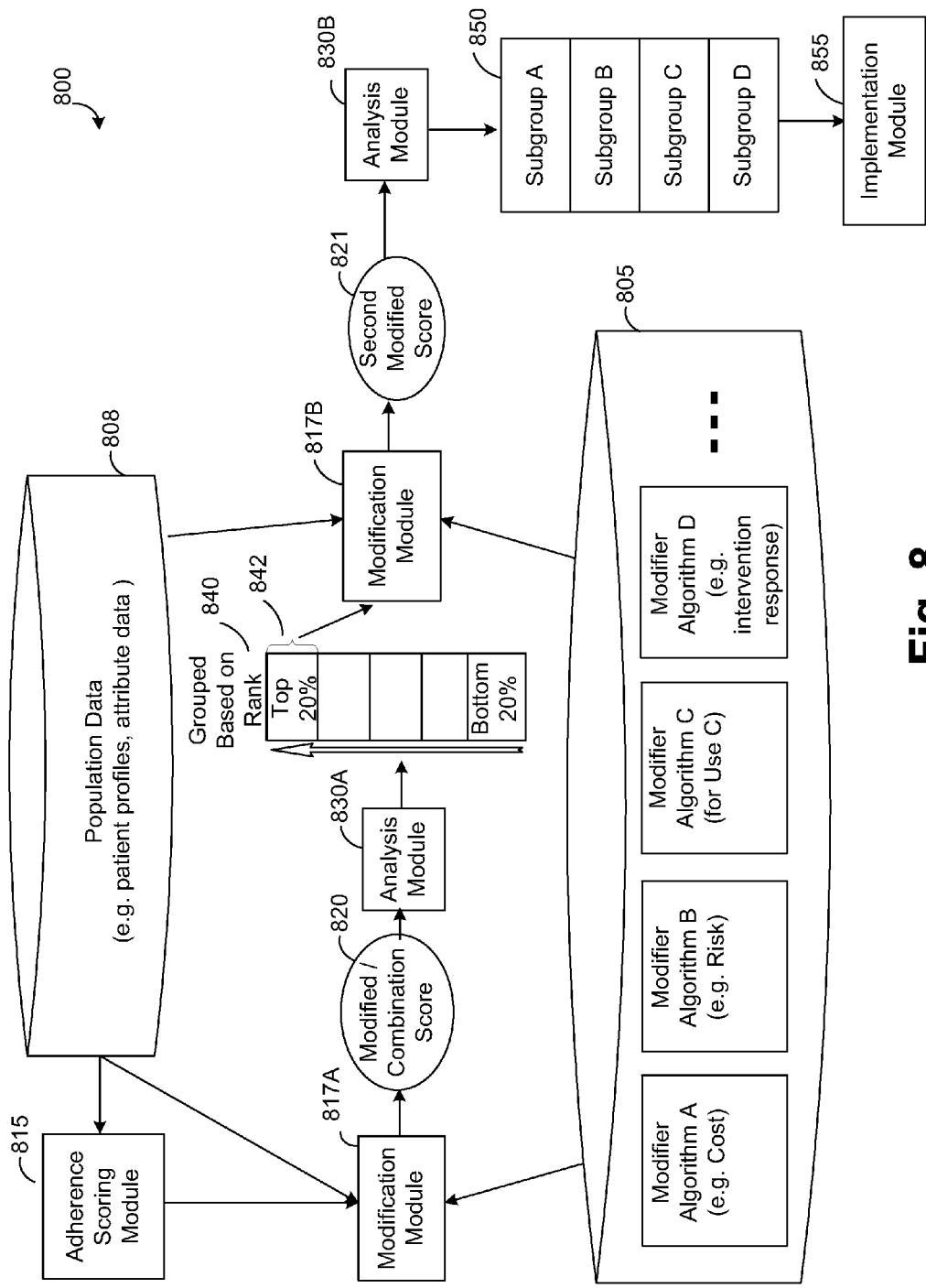
FIG. 8 shows an example of modifying patient adherence scores and of implementing an intervention based on those scores.

FIG. 8 shows an example of modifying patient adherence scores and of implementing an intervention based on those scores. A data storage device 805 stores one or more modifier algorithms. A second data storage device 808 stores population data including patient profiles for multiple patients. In some examples, the modifier algorithms can be stored in the same storage device as the population data. Multiple patient profiles are supplied to an adherence scoring module 815 where each profile is assigned a patient adherence score. A modification module 817A can obtain the patient profiles and their adherence scores from the adherence scoring module 815. The modification module 817 can also obtain the same patient profiles from the data storage device 808. The modification module can also obtain a first modifier algorithm (e.g. Modifier Algorithm A) from the data storage device 805. The modification module can determine a modifier for each of the patient profiles using the first modifier algorithm obtained from the data storage device 805. Optionally, the modification module can obtain a second modifier algorithm (e.g. Modifier for Algorithm B), from the data storage device 805. Using the second modifier, the modification module can determine a second modifier for each of the patient profiles. The modification module 817A applies the one or modifiers for each patient profile to modify each of the respective patient adherence scores assigned to the patient profiles into a modified score 820. Any number of modifier algorithms can be stored and used by the modification module 817A. The modified scores 820 and the patient profiles are supplied to an analysis module 830A for analysis. The patient profiles are indexed based on their respective modified scores and grouped into multiple groups. A graphical representation of an index 840 shows the patient profiles ranked from lowest to highest and grouped based on the modified score, group 842 includes the top 20% of patient profiles based on a rank in the index.

The patient profiles, the original adherence score, and the modified scores 820 for one of the groups 842 (e.g. the top 20 percent) can be obtained by a modification module 817B. The patient profiles can be supplied along with the ranking and modified scores. In other examples, additional patient data the can be obtained from the data storage device 808. The modification module 817B can be the same modification module as modification module 817A. The modification module 817B can obtain a modifier algorithm e.g. Algorithm D from the data storage device 805 and use that modifier algorithm to determine an additional modifier for each of the patient profiles to modify the patient adherence score or the modified score into a second modified score 821. An analysis module 830B can then be used to further sub-group the patients (or the patient profiles) based on the second modified score 821. A graphical representation of the sub-grouping is shown at 850. Also, based on the sub-grouping an implementation module 855 can implement various protocols based on the sub-grouping such as, adjusting premiums, producing reports, implementing an automated intervention regime, or implementing a disease management program etc.

As shown in FIG. 8, Modifier Algorithms A and B can be algorithms for determining modifiers for cost and risk, respectively. The modification module 817A can determine a cost and a risk modifier for each of the patient profiles and then modify each of the patient adherence scores for multiple patient profiles in a patient population to obtain a combination score 820 for each of the profiles indicating the cost and risk of each patient. The analysis module 830A can stratify and group the patients in the population based on the combination score. The modification module 817B can obtain an intervention modifier algorithm, Modifier Algorithm D, from the data storage device 805 and modify each of the adherence scores into a second modified score 821 for the patient profiles in one of the groups 842 by applying the intervention modifier to the patients in that group. In this example, the second modified score 821 indicates the likelihood of various interventions to increase adherence among patients in the group 842. The analysis module 830B can further sub-group the patients (or the patient profiles) based on the second modified score 821 into sub-groups shown at 850 for each type of intervention. For example, the patients most likely to respond to a first intervention (e.g. automated email) can be grouped into Sub-group A; patients most likely to respond to an economic incentive can be grouped in Sub-group B, etc. The sub-groups can be provided to the implementation module 855 for implementing the various types of interventions for each of the sub-groups. In this manner, intervention can be tailored to the highest-risk and highest cost patients in a population to increase their adherence.

In some examples, the data storage device can have multiple intervention algorithms, each for a different type of intervention. The modification module 817B can use one of the intervention algorithms to determine a modifier and adjust the modified score for each of the patient profiles into a second modified score for a first type of intervention. The analysis module 830B can then select the patient profiles with the highest scores and group them in a first group, e.g. Group A for the first type of intervention. The modification module 817B can use another of the intervention algorithms for a second type intervention to determine a modifier for the second type of intervention and to adjust the modified score for each of the patient profiles into a second modified score 821 for the second type of intervention. The analysis module 830B can then select the patient profiles with the highest scores and group them in a second group, e.g. Group B for the second type of intervention. In this manner, the analysis module can group patient profiles into groups based on the most effective type of intervention for those patients. At 855, the implementation module can implement the first intervention for group A and the second intervention for Group B etc.

Combination adherence scores can be used for various applications including for clinical trial research. In order to increase retention rate and decrease clinical trial times, a modifier can be used at the time of enrollment to help identify candidates most likely to be adherent to a prescribed treatment. Such modifiers can also be used with an intervention modifier to increase enrollment and/or retention rate. To increase enrollment number and retention rate, a combination modifier can help determine which candidates with less than ideal adherence scores are the most likely to respond to intervention. A modification algorithm for adherence among patients with the disease that is the subject of the clinical trial and a modifier algorithm for intervention can be used to determine a disease specific modifier and an intervention modifier for each of the multiple patient profiles of potential clinical trial patients. The modifiers for each of the multiple patient profiles can be used to modify adherence scores obtained for the patient profiles in order to determine which patients will be adherent, which will not be adherent, which patients will respond to intervention, and which patients will not respond to intervention. In this manner, the effectiveness of a clinical trial can be improved by eliminating patients with low likelihood of adherence and who will not respond to intervention. Also, during the clinical trial, resources can be devoted to monitoring those patients who have the lowest likelihood of adherence.

Multiple modifiers can also be used for modeling patient adherence in a patient population in order to determine benefit design. Modifiers for patient risk and cost and for predicting adherence for a specific disease can be used to predict the comparative effectiveness of various benefits. Accordingly, benefit design can be structured to have the greatest impact on quality and cost.

In another example, multiple modifiers can be used for discharge planning A modifier for risk, a modifier for adherence based on a specific disease, and a modifier for interventions can be used together to determine what interventions will be effective after a patient is discharged. In like manner, an adherence modifier for a patient's disease and for a particular drug can be used to determine if a particular prescription used in the hospital should be changed prior to the patients discharge. For example, some patients' risk of non-adherence can be decreased by changing to a simpler prescription regime than was used while admitted to a hospital.

Figure 9:
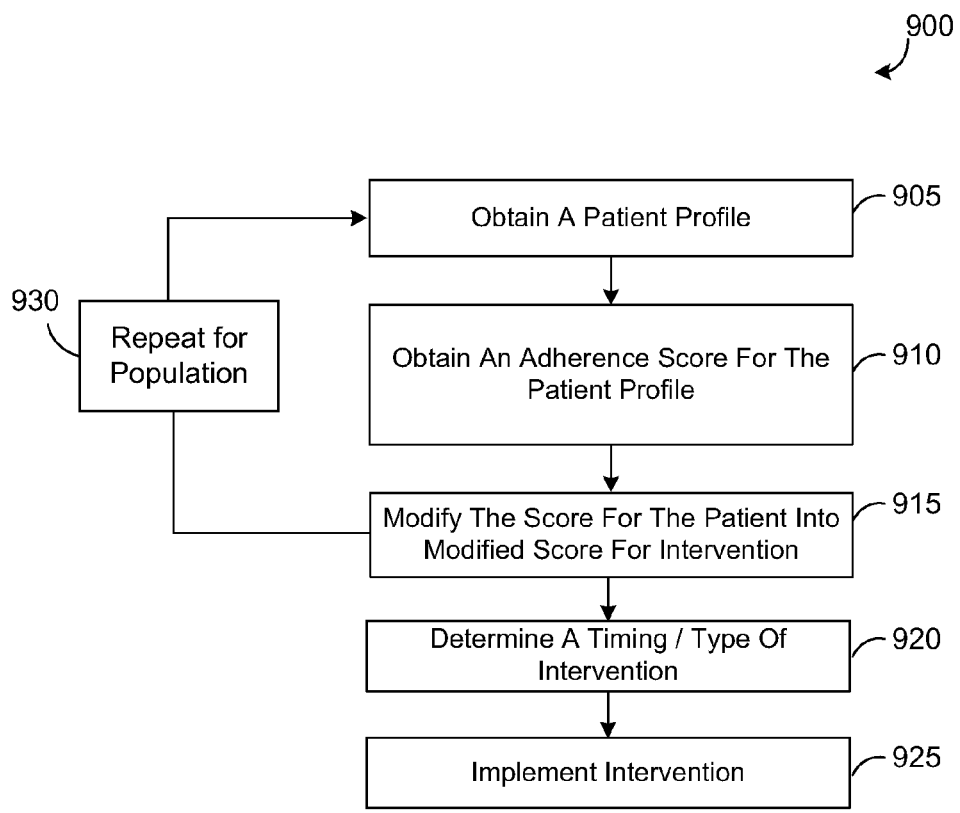
FIG. 9 shows an example of a process for modifying an adherence score.

FIG. 9 shows an example of a process 900 for modifying an adherence score. At 905, the process 900 obtains a patient profile for a patient, e.g. from a data storage device. The patient profile includes multiple patient attributes, each patient attribute including a value. At 910, the process 900 obtains an adherence score for the patient profile. The adherence score indicates a likelihood of the patient to be adherent to a prescription.

At 915 the score is modified into a modified score for intervention using an algorithm for modifying the score into a score for determining an intervention. A modifier algorithm for intervention can include a set of weights that are used to weight a particular set of attributes of the patient profile. For example, for the patient profile, a modifier can be determined based on the weights of the algorithm and the attribute values associated with the attributes in the patient profile. The modifier can be used to adjust the adherence score for the patient profile into a modified score for intervention such as to indicate a type of intervention, a timing of intervention, and/or whether/how a patient should be included in an intervention campaign.

At 920, a type and/or timing of an intervention is determined for the patient profile. The modified score for the patient profile can indicate a likelihood of the patient to respond to an intervention type and/or timing of intervention. A high modified score can indicate a higher likelihood of response to a particular intervention type and/or timing of intervention, and a lower score can indicate a lower likelihood of response. In some examples, a patient that has a high adherence score (i.e., indication that the patient will likely be adherent to a prescription) may have a relatively low likelihood of changing adherence behavior with repeated intervention such as repeated emails, phone calls, etc. As a result, the patient's modified score for intervention can be relatively low indicating low likelihood of response to such intervention. For such a patient, a low-frequency, low cost intervention can be implemented to not consume resources, such as high costs associated with greater intervention intensity.

Also, other patient attributes, such as disease severity, when included in the algorithm for modifying the adherence score can further increase or decrease the modified score. The same patient's modified score for intervention can increase due to a high disease severity of the patient, indicating that the patient is a higher risk patient; as a result, a more frequent or more direct intervention can be determined for the patient to ensure a more strict compliance with a prescription.

At 925, the determined intervention is implemented. The intervention can be implemented by an automated system for making emails, phone calls, text messages, and the like. The automated system can also direct a health care professional, such as a doctor, nurse, pharmacist etc., to intervene, such as through a phone call or through scheduling an office visit.

In some examples, timing and type of intervention can be determined separately at 920. For example, an adherence score for the patient profile can be modified for a particular type of intervention to produce a modified score indicating the likely effectiveness of a particular type of intervention for the patient associated with the patient profile. If the patient associated with the profile is selected for the particular type of intervention, the patient's adherence score (or modified adherence score) can be further modified into a modified adherence score for determining the best timing for the intervention for the patient.

At 930, modifying the adherence score can be repeated for multiple patients. For example, a profile at 905 and an adherence score at 910 can be obtained for each of multiple patients in a patient population. At 915, the adherence score for each of the patients in the population can be modified into a modified score for intervention. At 920, timing and/or type of intervention can be determined for some or all of the patients in the population. For example, the modified adherence scores for the patients in the patient population can be for a particular type of intervention. In other words, the modified adherence score for a patient in the population can indicate the likely effectiveness of the particular type of intervention for the patient. The patients in the population can be stratified according to the modified adherence score. It can be determined that only a subset of the population, e.g. those having a modified score above a threshold, will receive the particular intervention. The threshold can be determined based on budget for an intervention campaign that includes the particular type of intervention.

Also, the adherence scores for the patients in the patient population can be modified a second time into second modified scores for a different type of intervention. The patients in the population can be re-stratified according to the second modified scores and combined to determine groups in the population likely to respond to the second type of intervention. In this manner, an intervention campaign can be determined for effectively altering the adherence behavior of patients in a patient population while minimizing the costs of the campaign.

In some implementations, an adherence score or a modified adherence score can be used to complete a HRA. A HRA includes one or more questions that can be used to determine a HRA score for a particular patient based on the patient's response(s) to the HRA question(s). The HRA score can indicate a likelihood of a particular event occurring for the patient. For example, a HRA score can indicate the likelihood of a particular clinical outcome for the patient such as hospitalization or an emergency room visit, likelihood of the patient to enroll in self-care, and likely medical cost for treating the patient.

In some examples, many patients in a patient population will not complete a HRA when the HRA is administered to the patient population. These patients are referred to herein as non-responders. Those who complete the survey are referred to as responders. Without HRA scores for all of the patients in the patient population, it can be difficult to profile the population such as for intervention and/or for underwriting.

Figure 10:
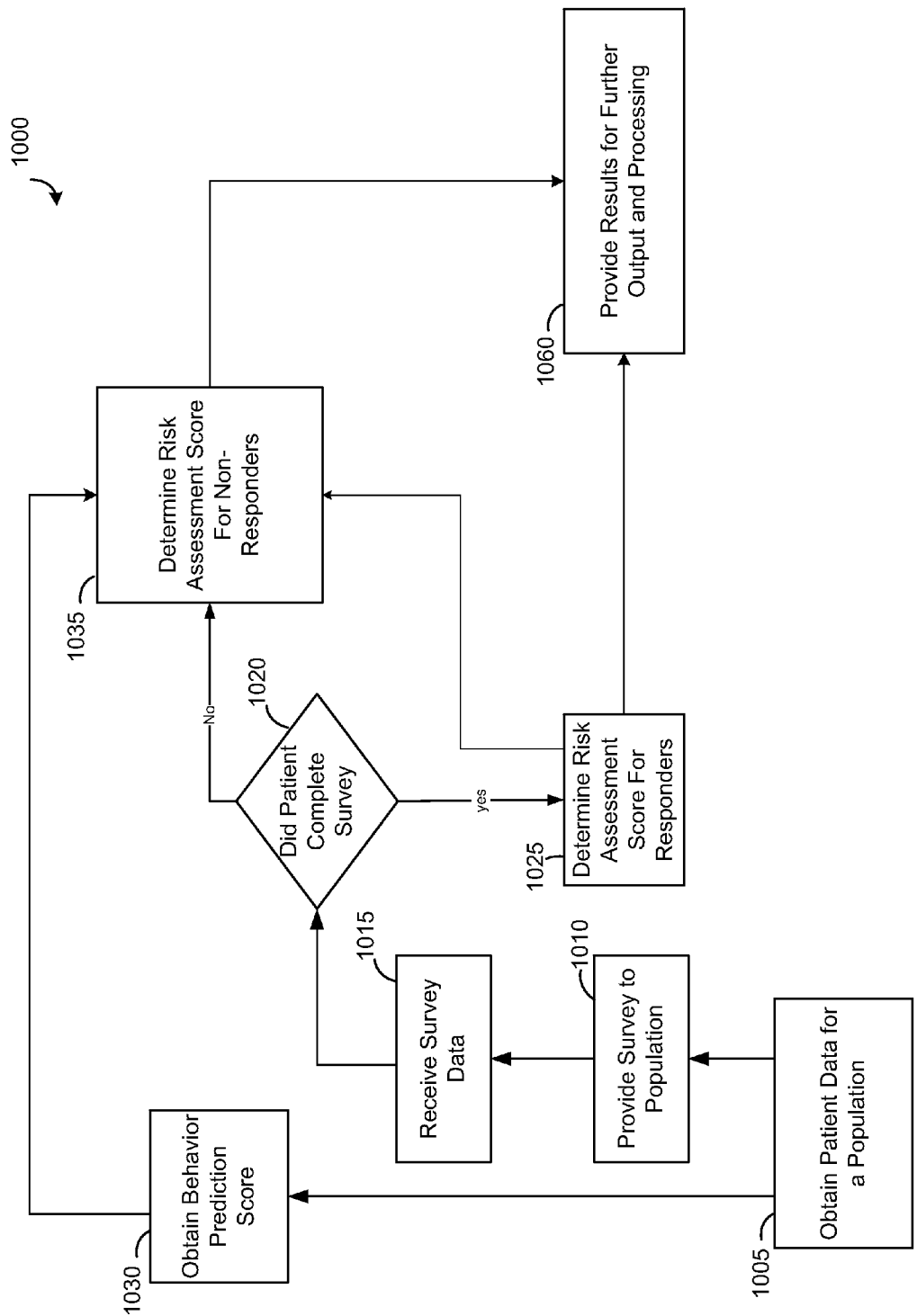
FIG. 10 shows an example of a process for obtaining HRA scores for a population of patients.

FIG. 10 shows an example of a process 1000 for obtaining HRA scores for a population of patients, including responders and non-responders. At 1005, patient data is obtained for a population of patients. A population of patients can be defined based on a common characteristic amongst the patients. For example, all of the patients having a common disease can be included in a population. In some examples, all of the patients of a physician or group of physicians can be included in a patient population. In some examples, all of the patients in a particular health plan can be included in a patient population. The patient data can be actively retrieved such as from one or more data storage devices in a clinical management system. Also, the data can be obtained by passively receiving the data such as at a clinical management system. The clinical management system has one or more processors that can perform the operations of the process 1000.

At 1010, a HRA is provided to the patient population. For example, the clinical management system can provide the HRA to the patients in the population electronically over a network such as through a computer console at the patient's physician's office, via email to the patient population, and/or via a website. At 1015, patient survey data is received from the patients and can be stored by the clinical management system in the one or more data storage devices. At 1020, it is determined which patients responded (responders) and which patients did not respond (non-responders). At 1025, HRA scores are determined for the responders based on their responses to the HRA.

Also, based on the patient data obtained for the patients in the patient population, a behavior prediction score, such as an adherence score or a modified adherence score, can be obtained at 1030 for the patients in the population, including responders and non-responders. The behavior prediction score can be obtained from a data storage device. For example, the data can be actively retrieved from a data storage device. In some examples, the data can be passively received The data storage device can include behavior prediction scores that have been determined based on patient attribute data for the patients in the population.

Based on the obtained behavior prediction scores for the non-responders and the responders and based on the determined HRA scores for the responders obtained at 1025, a HRA score can be determined for the non-responders at 1035. For example, a non-responder can be mapped to multiple responders by matching a behavior prediction score of the non-responder to the behavior prediction score of the responders. Matching can include identifying scores that are identical; it can also include identifying scores that fall within a range, such as a predefined margin. A combined HRA score for the non-responder can be determined by combining the HRA scores of all of the matching responders. The combined risk assessment score can be determined by averaging all of the HRA scores of the matching responders. The combined score is assigned to the non-responder. The discussion below in connection with FIGS. 11-16 provides more details and examples of how a risk assessment score can be obtained for a non-responder. The HRA scores for the responders and the non-responders can be provided at 1060 for further output and/or processing.

Further processing can include, for example, determining an appropriate intervention for the responders and non-responders. To determine an appropriate intervention, the patients can be ranked from low to high risk based on their HRA scores. A predetermined threshold can be used to identify patients who should be enrolled in a wellness program. The patients whose risk assessment score is above the predetermined threshold can be identified for a particular intervention such as a wellness program. In some examples, the responders and the non-responders can each be ranked separately. A different threshold can be used for the responders than is used for the non-responders because the risk assessment score for the responders is derived directly from an HRA whereas the HRA scores for the non-responders are imputed based on behavior prediction scores and therefore may have differing predictive value.

In some examples, after the patients, including responders and non-responders, have been ranked based on their HRA scores, a group of the patients, such as the highest risk patients, can be reclassified based on another behavior prediction score, such as a modified adherence score, obtained for the patients in that group. For example, once the high risk patients have been identified based on the ranking, those patients can be reclassified based on a modified adherence score for those patients to determine an appropriate timing and/or method of intervention. Also, the reclassification can be performed separately for the responders and the non-responders as the analysis for determine timing and/or method of intervention may differ for responders and non-responders.

Output and processing at 1060 can also include, for example, using the HRA scores for the responders and the non-responders to adjust underwriting such as for a health care plan. The HRA scores for the responders and the non-responders of patients in a health plan can be aggregated to determine a total risk for the health plan. Based on the aggregated HRA score, a health plan's underwriting can be adjusted accordingly.

Figure 11:
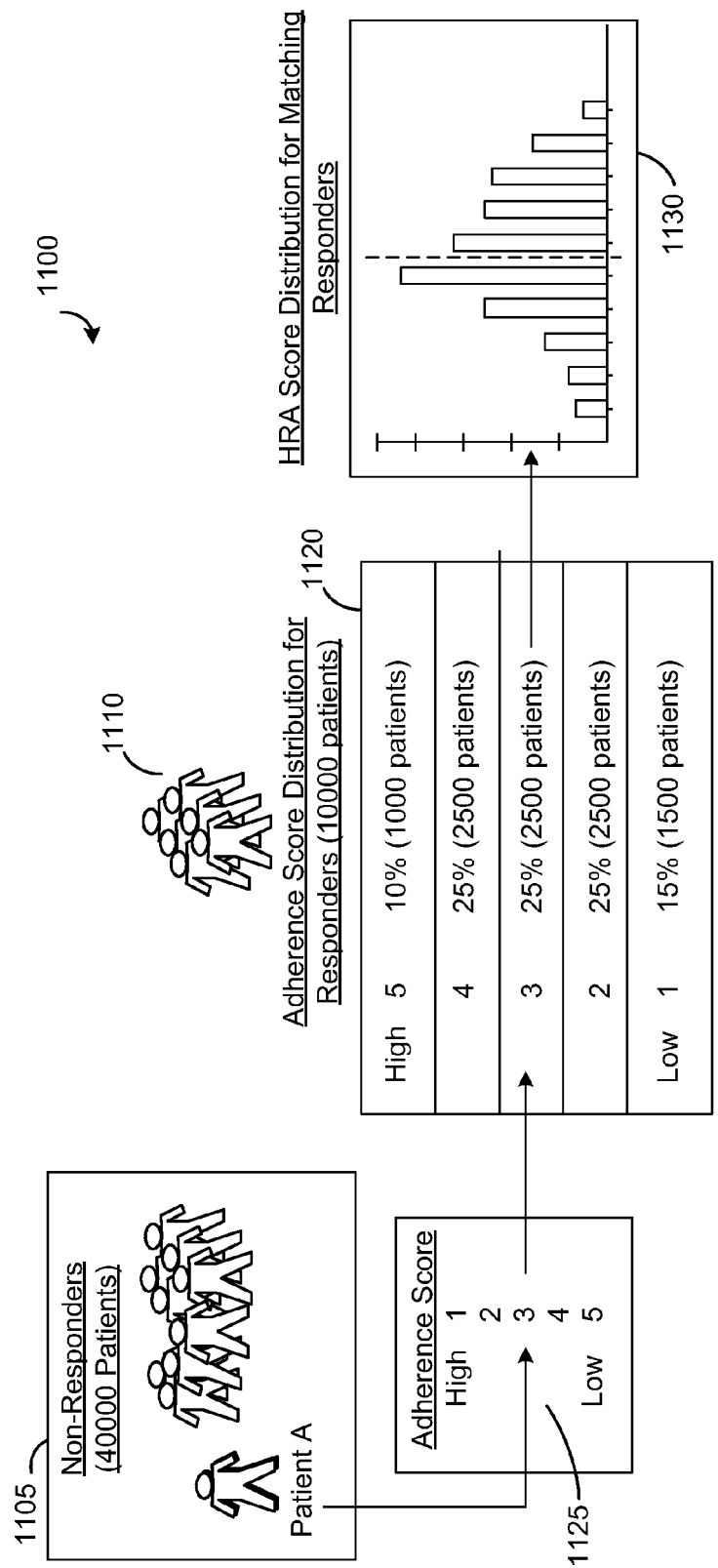
FIG. 11 shows an example of a schematic of determining an HRA score for a non-responder in a patient population.

FIG. 11 shows an example of a schematic of determining an HRA score for a non-responder in a patient population. The patient population has 50,000 patients, including a group of non-responders 1105 with 40,000 patients, including Patient A. The patient population also includes responders 1110. The responders 1110 have 10,000 patients. Each of the patients in the population has an adherence score ranging from 1 to 5, 1 being the lowest adherence score, and 5 being the highest adherence score.

An example distribution of the responders based on adherence scores for the responders is shown at 1120. The distribution includes a ranking from low to high based on adherence score. Patients with an adherence score of 1 include 1,500 patients which is 15 percent of the responders; patients with an adherence score of 2 includes 2,500 patients (25% of the responders); patients with an adherence score of 3 includes 2,500 patients (25% of the responders); and patients with high adherence score of 5 includes 1,000 patients (10% of the responders).

Patient A of the non-responders has an adherence score of 3 as shown at 1125. Patient A is matched to responders having the same adherence score as Patient A. 2,500 responders have an adherence score that matches the adherence score of Patient A. Each of the 10,000 responders 1110 has a HRA score based on their responses to the HRA. An example HRA score distribution is shown at 1130 for all of the responders in the population that have an adherence score (an adherence score of 3) that matches the adherence score of patient A. The distribution is shown in more detail in FIG. 12.

Figure 12:
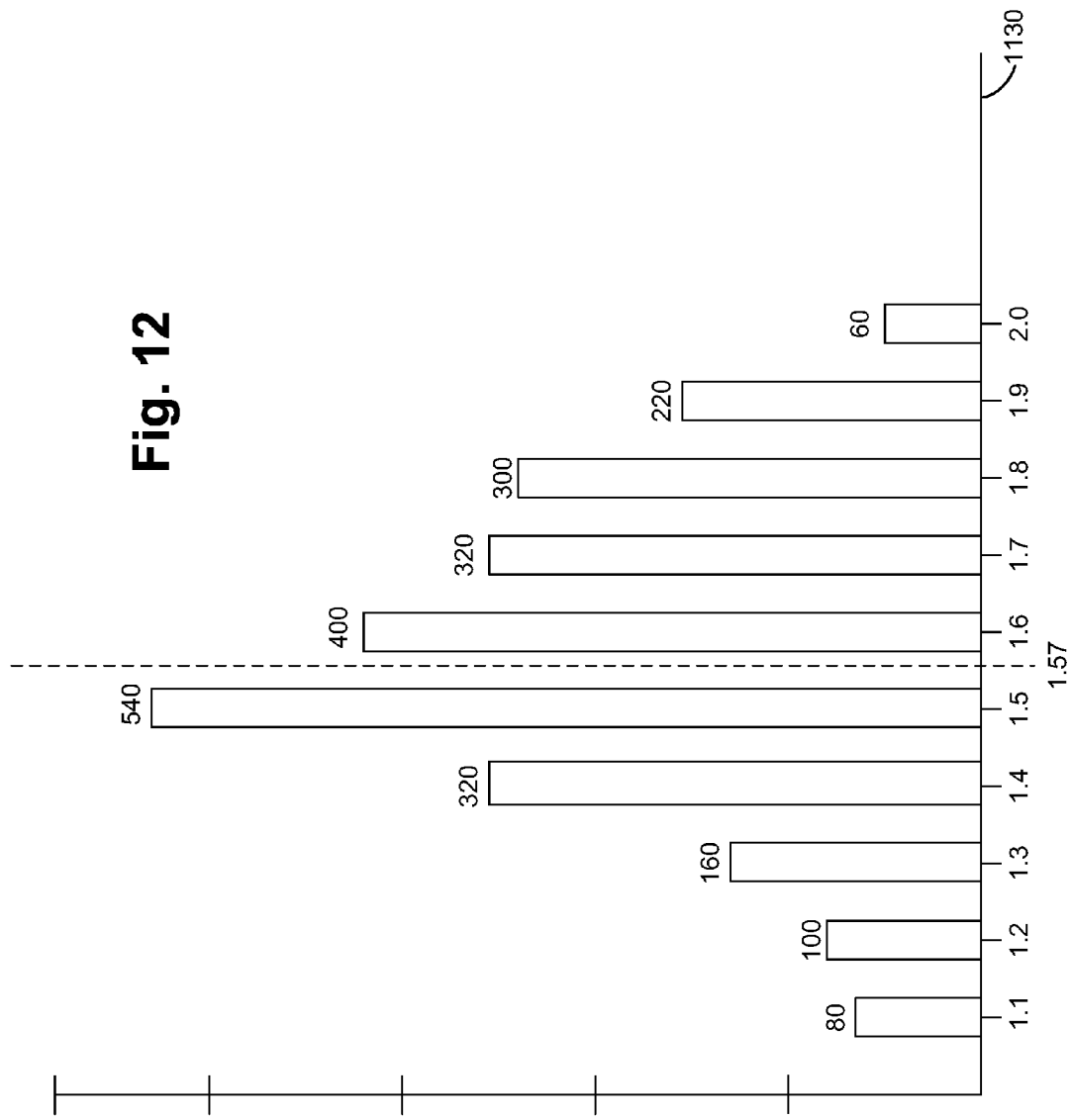
FIG. 12 shows an example of a distribution of HRA scores.

FIG. 12 shows an example of a distribution of HRA scores on the X-axis of the responders from FIG. 11 that have an adherence score matching the adherence score of Patient A. The Y-axis shows the number of matching responders having an HRA score ranging from 1.1 to 2.0. The average HRA score for the matching responders is 1.57. Patient A can be assigned an HRA score of 1.57. In some examples, the median score can be assigned to Patient A. Each of the non-responders can be assigned an HRA score by matching their adherence score with adherence scores of the responders and combining the HRA scores of the matching responders.

Figure 13:
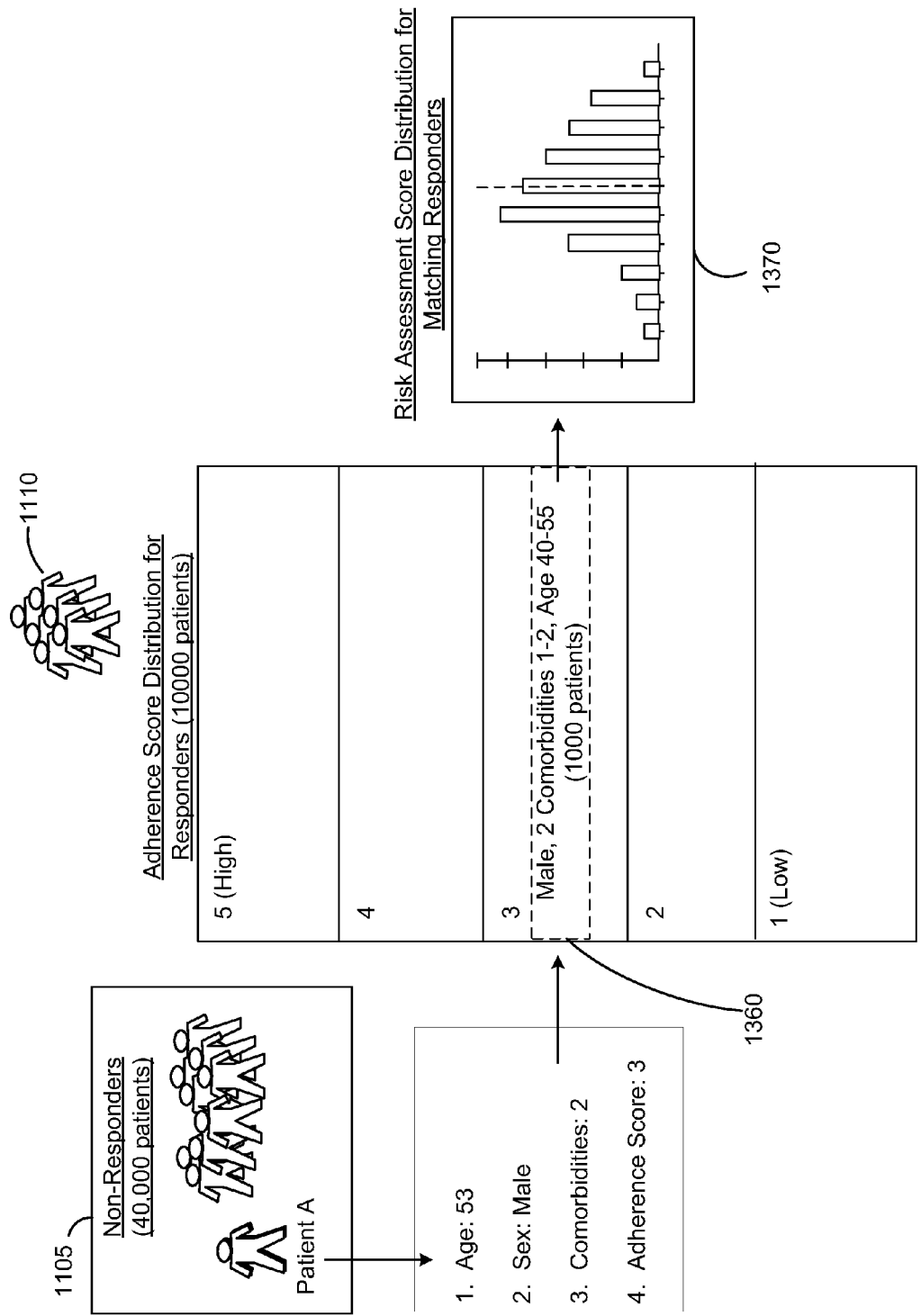
FIG. 13 shows an example of a schematic of determining a HRA score for a non-responder in the patient population.

FIG. 13 shows another example of a schematic of determining a HRA score for the non-responder, Patient A, in the patient population. The patient population has 50,000 patients, including the group of non-responders 1105 with 40,000 patients, including Patient A and the responders 1110 with 10,000 patients. In this example, a HRA score is determined for patient A based on adherence score and based on other attributes including Age, Gender, and Comorbidities. Attribute values for these attributes can be obtained from patient profiles stored in a data storage device for the patient population.

Various attributes can be indicators of the type of risk being assessed by the HRA. These attributes can be determined based on experiential data. FIG. 14 shows an example of a table of attributes that have been determined to be indicators of the type of risk being assessed by the HRA. Column A shows a list of attributes; Column B shows a range of attribute values for each attribute; and Column C shows a risk weight associated with the attribute values. Males for example have a risk weight of 1.1 whereas females have risk weight of 1.0 which indicates that males are generally higher risk for the type of risk than females. As for age, each age group has a different risk weight with patients 65 and over having a higher risk weight than the other ages. Also, comorbidities have a risk weight ranging from 1.0 for zero comorbidity to 2.0 for five or more comorbidities. Also, a risk weight can be determined for adherence score as well. With patients with a low adherence score having a high risk weight and patients with a high adherence score having a low risk weight.

Returning to FIG. 13, the attributes that were determined as indicators of the particular risk assessed by the HRA are used to determine a HRA score for Patient A, including age, gender, comorbidities, and adherence score. Responders who have attribute values that are within the same range as the attribute values of Patient A are identified. The matching responders are a subset 1360 of the responders; the subset includes those who have an adherence score of 3, who are male, who have 1-2 comorbidities, and who are age 40-55. This subset 1360 of responders includes 1000 patients who also have HRA scores based on their responses to the HRA. An example of a HRA score distribution is shown at 1370 for the subset 1360 of responders. This example of an HRA score distribution is shown in more detail in FIG. 15.

Figure 15:
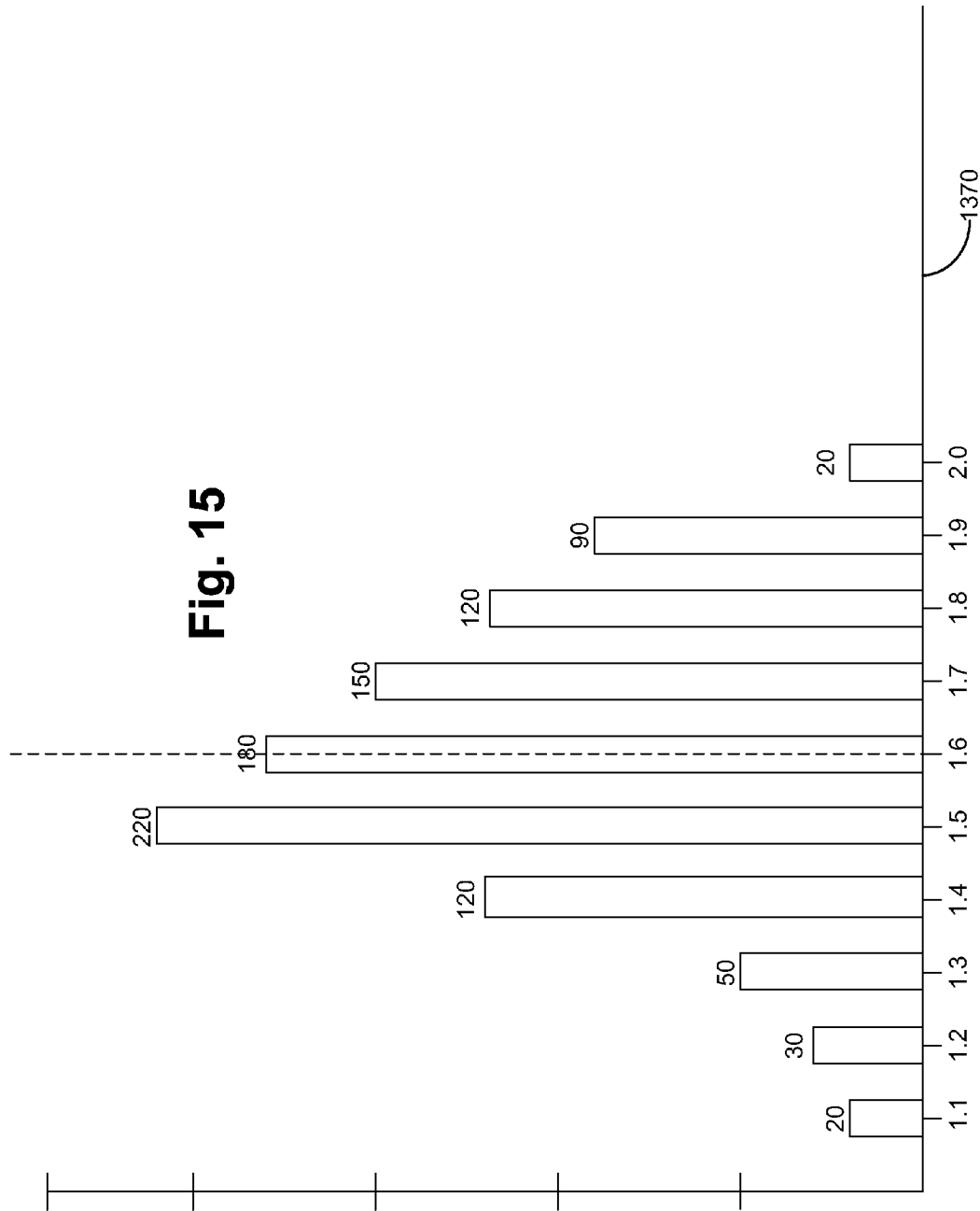
FIG. 15 shows an example of a distribution of HRA scores.

FIG. 15 shows an example of a distribution of HRA scores on the X-axis of the subset of responders 1360 from FIG. 13. The Y-axis shows a number of responders from the subset 1360 having an HRA score ranging from 1.1 to 2.0 (on the X-axis). The average HRA score for the subset of responders 1360 is 1.59. Patient A can be assigned an HRA score of 1.59. Each of the non-responders can be assigned a HRA score by matching their respective adherence scores and attribute values with adherence scores and attribute values of the responders and combining the HRA scores of the matching responders.

In the examples shown in FIGS. 11-15, determining an HRA score for a non-responder is discussed using adherence scores for the non-responder and for the responders. Instead of using an adherence score, a modified adherence score can also be used. For example, an adherence score for each of the patients in the population can be obtained. That adherence score can be modified for a particular application that is indicative of the type of risk being assessed by the HRA. For example, the adherence scores for the patients can be modified for the particular type of risk being assessed by the HRA using weights such as the risk weights discussed in connection with FIG. 14 to determine a modifier for adjusting the adherence score.

By modifying the adherence score, using risk weights, the affects different attributes have on each other can be captured in a modified adherence score. For example, the affect an attribute has on risk can be a function of other attributes. For example, the affect the number of comorbidities has on predicted risk can be a function of age. Patients older than 65 with 2-5 comorbidities can have a substantially higher predicted risk than patients ages 40-55 with 2-5 comorbidities. And, therefore, the weight associated with comorbidities can be adjusted according to age. By modifying the adherence score for the patients in the patient population and then matching modified adherence scored to determine an HRA for a non-responder, a more accurate determination of the non-responders HRA score can be made.

Figure 16:
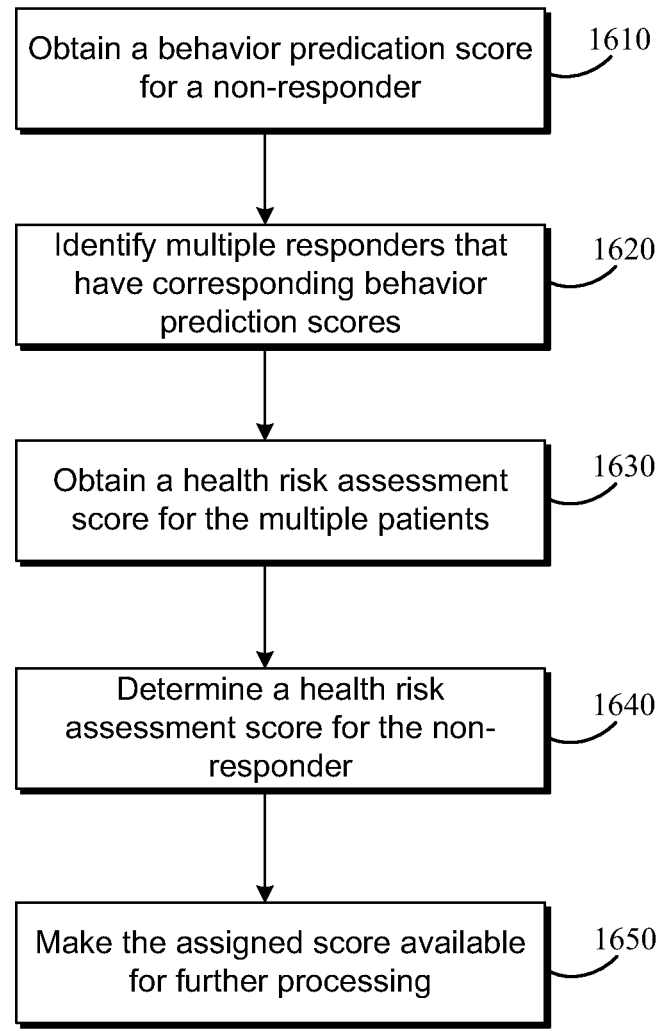
FIG. 16 shows an example of a process for determining a HRA score for a non-responder in patient population Like reference symbols in the various drawings indicate like elements.

FIG. 16 shows an example of a process for determining a HRA score for a non-responder in patient population having responders and non-responders. At 1610, a behavior prediction adherence score is obtained for the non-responder in the population based on a patient profile for the patient stored in a data storage device. The obtaining can include, for example, receiving the behavior prediction score. Also, the obtaining can be an active step whereby a behavior prediction score is retrieve or determined. The behavior prediction score can be obtained by weighting various patient attributes in the patient profile. At 1620, responders from the patient population are identified from patient data in a data storage device that have behavior prediction scores that correspond the behavior prediction score for the non-responder. Scores that correspond can include scores that match, or scores that fall within a margin of scores. At 1630, a HRA score is obtained for each of the responders based on the respective HRAs completed by the responders. The HRA score can be passively received, actively retrieved from e.g., a data storage device, or determine based on the responder's responses the HRAs. At 1640, an HRA score is determine for the non-responder based on the HRA scores of the responders that have corresponding behavior prediction scores. The HRA scores for responders that correspond can be combined into a combined HRA score such as by determining a mean of the HRA scores for the responders. The combined score can be assigned to the non-responder. At 1660, the determined score is made available for further processing an output.

The process can be repeated for each of the non-responders in a population to obtain HRA scores for each of the non-responders. The HRA scores for the total population include responders and non-responders can be made available for further processing such as profiling the population to determine appropriate interventions or to adjust underwriting.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on a computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), peer-to-peer networks (e.g., ad hoc peer-to-peer networks), wireless networks, mobile phone networks etc.

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Particular implementations have been described in this document. Variations and enhancements of the described implementations and other implementations can be made based on what is described and illustrated in this document. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A computer-implemented method for modifying a patient adherence score, comprising:

obtaining patient profiles from one or more computer-readable storage devices for a patient population, wherein each patient profile from among the obtained patient profiles includes multiple attribute values for multiple attributes for a patient from the patient population who is associated with the patient profile;

for each patient profile of the obtained patient profiles, determining, by a computer system, an associated behavior prediction score based on the multiple attribute values, wherein the associated behavior prediction score is a predictor of a relative likelihood of a behavior for a patient from the patient population who is associated with the patient profile;

accessing, from among the determined behavior prediction scores, a behavior prediction score for a patient from the patient population who did not complete a health risk assessment;

identifying, by the computer system from the patient population, multiple patients who did respond to the health risk assessment and have behavior prediction scores that correspond to the behavior prediction score for the patient who did not complete the health risk assessment;

obtaining, by the computer system, health risk assessment scores for the multiple patients based on the respective health risk assessments completed by the multiple patients, the health risk assessment scores indicating risks being assessed by the health risk assessment;

determining, by the computer system, a health risk assessment score for the patient who did not complete the health risk assessment by combining the health risk assessment scores of at least some of the multiple patients; and making the determined health risk assessment score available for further processing and output.

2. The computer implemented method of claim 1, wherein the combining comprises averaging the health risk assessment scores for the multiple patients.

3. The computer implemented method of claim 1, further comprising:

repeating the accessing the behavior prediction score, the determining the health risk assessment score, and the making available the determined health risk assessment score for multiple other patients who did not complete the health risk assessment;

ranking, by the computer system, the patients who did not complete the health risk assessment based on the determined health risk assessment scores; and determining a subset of the multiple patients who did not complete the health risk assessment to receive an intervention based on the ranking.

4. The computer implemented method of claim 1, further comprising:

identifying, by the computer system, a group of patients from among the multiple patients, wherein patients in the identified group have attribute values that correspond to attribute values for the patient who did not complete the health risk assessment, and wherein said determining the health risk assessment score for the patient who did not complete the health risk assessment is performed by combining the health risk assessment scores of patients in the identified group.

5. The computer implemented method of claim 1, wherein the relative likelihood of the behavior comprises a likelihood to adhere to a prescribed treatment, and the behavior prediction score comprises an adherence score that indicates a likelihood of adherence of the patient to a prescribed treatment.

6. The computer implemented method of claim 5, further comprising modifying, by the computer system, the adherence score into a modified score for a particular application based on a set of weights for weighting the multiple patient attribute values in the patient profile.

7. The computer implemented method of claim 6, wherein the multiple attributes comprise a first attribute having a first value and a second attribute having a second value, the first attribute indicative of the risk being assessed based on the value of the second attribute; and the modifying the adherence score comprises determining a modifier for adjusting the adherence score by applying a weight to the first value, the weight a function of the second value.

8. A non-transitory computer-readable storage medium storing instructions, which, when executed by a processor, causes the processor to perform operations comprising:

obtaining patient profiles from one or more computer-readable storage devices for a patient population, wherein each patient profile from among the obtained patient profiles includes multiple attribute values for multiple attributes for a patient from the patient population who is associated with the patient profile;

for each patient profile of the obtained patient profiles, determining an associated behavior prediction score based on the multiple attribute values, wherein the associated behavior prediction score is a predictor of a relative likelihood of a behavior for a patient from the patient population who is associated with the patient profile;

accessing, from among the determined behavior prediction scores, a behavior prediction score for a patient from the patient population who did not complete a health risk assessment;

identifying, from the patient population, multiple patients who did respond to the health risk assessment and have behavior prediction scores that correspond to the behavior prediction score for the patient who did not complete the health risk assessment;

obtaining health risk assessment scores for the multiple patients based on the respective health risk assessments completed by the multiple patients, the health risk assessment scores indicating risks being assessed by the health risk assessment;

determining a health risk assessment score for the patient who did not complete the health risk assessment by combining the health risk assessment scores of at least some of the multiple patients; and making the determined health risk assessment score available for further processing and output.

9. The non-transitory computer-readable storage medium of claim 8, wherein the operation of combining comprises averaging the health risk assessment scores for the multiple patients.

10. The non-transitory computer-readable storage medium of claim 8, the operations further comprising:

repeating the operations of accessing the behavior prediction score, determining the health risk assessment score, and making available the determined health risk assessment score for multiple other patients who did not complete the health risk assessment;

ranking the patients who did not complete the health risk assessment based on the determined health risk assessment scores; and determining a subset of the multiple patients who did not complete the health risk assessment to receive an intervention based on the ranking.

11. The non-transitory computer-readable storage medium of claim 8, the operations further comprising:

identifying a group of patients from among the multiple patients, wherein patients in the identified group have attribute values that correspond to attribute values for the patient who did not complete the health risk assessment, and wherein the operation of determining the health risk assessment score for the patient who did not complete the health risk assessment is performed by combining the health risk assessment scores of patients in the identified group.

12. The non-transitory computer-readable storage medium of claim 8, wherein the relative likelihood of the behavior comprises a likelihood to adhere to a prescribed treatment, and the behavior prediction score comprises an adherence score that indicates a likelihood of adherence of the patient to a prescribed treatment.

13. The non-transitory computer-readable storage medium of claim 12, the operations further comprising modifying the adherence score into a modified score for a particular application based on a set of weights for weighting the multiple patient attribute values in the patient profile.

14. The non-transitory computer-readable storage medium of claim 13, wherein
the multiple attributes comprise a first attribute having a first value and a second attribute having a second value, the first attribute indicative of the risk being assessed based on the value of the second attribute; and
the operation of modifying the adherence score comprises determining a modifier for adjusting the adherence score by applying a weight to the first value, the weight a function of the second value.

15. A system comprising:
one or more hardware processors; and
a non-transitory computer-readable medium storing instructions that, when performed by the one or more hardware processors, cause the system to perform operations comprising:
obtaining patient profiles from one or more computer-readable storage devices for a patient population, wherein each patient profile from among the obtained patient profiles includes multiple attribute values for multiple attributes for a patient from the patient population who is associated with the patient profile;
for each patient profile of the obtained patient profiles, determining an associated behavior prediction score based on the multiple attribute values, wherein the associated behavior prediction score is a predictor of a relative likelihood of a behavior for a patient from the patient population who is associated with the patient profile;
accessing, from among the determined behavior prediction scores, a behavior prediction score for a patient from the patient population who did not complete a health risk assessment;
identifying, from the patient population, multiple patients who did respond to the health risk assessment and have behavior prediction scores that correspond to the behavior prediction score for the patient who did not complete the health risk assessment;
obtaining health risk assessment scores for the multiple patients based on the respective health risk assessments completed by the multiple patients, the health risk assessment scores indicating risks being assessed by the health risk assessment;
determining a health risk assessment score for the patient who did not complete the health risk assessment by combining the health risk assessment scores of at least some of the multiple patients; and
making the determined health risk assessment score available for further processing and output.

16. The system of claim 15, wherein the operation of combining comprises averaging the health risk assessment scores for the multiple patients.

17. The system of claim 15, the operations further comprising:
repeating the operations of accessing the behavior prediction score determining the health risk assessment score, and making available the determined health risk assessment score for multiple other patients who did not complete the health risk assessment;
ranking the patients who did not complete the health risk assessment based on the determined health risk assessment scores; and
determining a subset of the multiple patients who did not complete the health risk assessment to receive an intervention based on the ranking.

18. The system of claim 15, the operations further comprising:
identifying a group of patients from among the multiple patients, wherein patients in the identified group have attribute values that correspond to attribute values for the patient who did not complete the health risk assessment, and
wherein the operation of determining the health risk assessment score for the patient who did not complete the health risk assessment is performed by combining the health risk assessment scores of patients in the identified group.

19. The system of claim 15, wherein
the relative likelihood of the behavior comprises a likelihood to adhere to a prescribed treatment, and
the behavior prediction score comprises an adherence score that indicates a likelihood of adherence of the patient to a prescribed treatment.

20. The system of claim 19, the operations further comprising modifying the adherence score into a modified score for a particular application based on a set of weights for weighting the multiple patient attribute values in the patient profile.

21. The system of claim 20, wherein
the multiple attributes comprise a first attribute having a first value and a second attribute having a second value, the first attribute indicative of the risk being assessed based on the value of the second attribute; and
the operation of modifying the adherence score comprises determining a modifier for adjusting the adherence score by applying a weight to the first value, the weight a function of the second value.

* * * * *

UNITED STATES PATENT AND TRADEMARK OFFICE
CERTIFICATE OF CORRECTION

| | | |
|---|---|---|
| PATENT NO. | : 8,676,607 B2 | Page 1 of 1 |
| APPLICATION NO. | : 12/987993 | |
| DATED | : March 18, 2014 | |
| INVENTOR(S) | : Bimal Vinod Patel et al. | |

It is certified that error appears in the above-identified patent and that said Letters Patent is hereby corrected as shown below:

Title Page, Column 1, under (73) Assignee, after "Inc." insert -- (US) --.

In the Claims

Column 32, line 7, in claim 17, delete "score" and insert -- score, -- therefor.

Signed and Sealed this
Twenty-fourth Day of June, 2014

Michelle K. Lee
*Deputy Director of the United States Patent and Trademark Office*